US007521421B2

(12) United States Patent
Naicker et al.

(10) Patent No.: US 7,521,421 B2
(45) **Date of Patent: *Apr. 21, 2009**

(54) DEUTERATED CYCLOSPORINE ANALOGS AND METHODS OF MAKING THE SAME

(75) Inventors: Selvaraj Naicker, Edmonton (CA); Randall W. Yatscoff, Edmonton (CA); Robert T. Foster, Edmonton (CA)

(73) Assignee: Isotechnika Inc., Edmonton (CA)

( * ) Notice: Subject to any disclaimer, the term of this patent is extended or adjusted under 35 U.S.C. 154(b) by 60 days.

This patent is subject to a terminal disclaimer.

(21) Appl. No.: 11/280,666

(22) Filed: Nov. 15, 2005

(65) Prior Publication Data

US 2006/0135414 A1 Jun. 22, 2006

Related U.S. Application Data

(63) Continuation of application No. 10/319,835, filed on Dec. 16, 2002, now abandoned, which is a continuation of application No. 09/634,945, filed on Aug. 7, 2000, now Pat. No. 6,613,739, which is a continuation of application No. 09/184,109, filed on Nov. 2, 1998, now abandoned, which is a continuation of application No. PCT/IB98/01693, filed on Oct. 8, 1998.

(60) Provisional application No. 60/061,360, filed on Oct. 8, 1997.

(51) Int. Cl.
*A61K 38/00* (2006.01)

(52) U.S. Cl. ......................... 514/11; 530/321; 530/350; 530/363; 530/806; 530/807

(58) Field of Classification Search ....................... None
See application file for complete search history.

(56) References Cited

U.S. PATENT DOCUMENTS

| | | | |
|---|---|---|---|
| 4,108,985 | A | 8/1978 | Rüegger et al. |
| 4,117,118 | A | 9/1978 | Härri et al. |
| 4,160,452 | A | 7/1979 | Theeuwes |
| 4,177,188 | A | 12/1979 | Hansen |
| 4,201,771 | A | 5/1980 | Onishi et al. |
| 4,210,581 | A | 7/1980 | Rüegger et al. |
| 4,220,641 | A | 9/1980 | Traber et al. |
| 4,256,108 | A | 3/1981 | Theeuwes |
| 4,265,874 | A | 5/1981 | Bonsen et al. |
| 4,288,431 | A | 9/1981 | Traber et al. |
| 4,289,851 | A | 9/1981 | Traber et al. |
| 4,384,996 | A | 5/1983 | Bollinger et al. |
| 4,396,542 | A | 8/1983 | Wenger |
| 4,404,194 | A | 9/1983 | Arala-Chaves |
| 4,554,351 | A | 11/1985 | Wenger |
| 4,639,434 | A | 1/1987 | Wenger et al. |
| 4,681,754 | A | 7/1987 | Siegl |
| 4,703,033 | A | 10/1987 | Seebach |
| 4,727,018 | A | 2/1988 | Eichner et al. |
| 4,764,503 | A | 8/1988 | Wenger |
| 4,765,980 | A | 8/1988 | DePrince et al. |
| 4,771,122 | A | 9/1988 | Seebach |
| 4,798,823 | A | 1/1989 | Witzel |
| 4,839,342 | A | 6/1989 | Kaswan |
| 4,866,036 | A | 9/1989 | Durette |
| 4,868,155 | A | 9/1989 | Durette |
| 4,868,157 | A | 9/1989 | Durette |
| 4,885,276 | A | 12/1989 | Witzel |
| 4,914,188 | A | 4/1990 | Dumont et al. |
| 4,963,362 | A | 10/1990 | Rahman et al. |
| 4,963,683 | A | 10/1990 | Avery et al. |
| 4,970,076 | A | 11/1990 | Horrobin |
| 4,996,193 | A | 2/1991 | Hewitt et al. |
| 4,997,648 | A | 3/1991 | Galpin et al. |
| 5,013,719 | A | 5/1991 | Bowlin |
| 5,047,512 | A | 9/1991 | Handschumacher et al. |
| 5,051,402 | A | 9/1991 | Kurihara et al. |
| 5,068,247 | A | 11/1991 | Fujita et al. |
| 5,079,341 | A | 1/1992 | Galpin et al. |
| 5,084,441 | A | 1/1992 | Shaw et al. |

(Continued)

FOREIGN PATENT DOCUMENTS

| | | |
|---|---|---|
| BE | 866810 | 11/1978 |
| CA | 2086267 | 6/1994 |
| CH | 630061 | 5/1982 |
| CH | 630062 | 5/1982 |
| CS | 8906499 | 8/1992 |

(Continued)

OTHER PUBLICATIONS

Curran, D., et al. "Intramolecular Hydrogen Transfer Reactions of *o*-(Bromophenyl)dialkylsilyl Ethers. Preparation of Rapamycin -$d_1$." *Tetrahedron Letters*. 33(17):2295-2298 (1992).

Eberle, M. K., et al. "Modifications of the MeBmt Side Chain of Cyclosporin A." *Bioorganic & Medicinal Chemistry Letters*. 5(15):1725-1728 (1995).

Hensens, O., et al. "The Preparation of [2-Deutero-3-Fluoro-D-ALA$^8$] Cyclosporin A By Directed Biosynthesis." *J. Antibiotics*. 45(1): 133-135 (1992).

Hughes, P. et al. "The Isolation, Synthesis and Characterization of An Isomeric Form of Rapamycin." *Tetrahedron Letters*. 33(33): 4739-4742 (1992).

Kobel, H., and R. Traber. "Directed Biosynthesis of Cyclosporins." *European Journal of Applied Microbiology and Biotechnology*. (14) 237-240 (1982).

(Continued)

*Primary Examiner*—Anish Gupta
(74) *Attorney, Agent, or Firm*—Fish & Richardson P.C.

(57) ABSTRACT

Cyclosporine derivatives are disclosed which possess enhanced efficacy and reduced toxicity over naturally occurring and other presently known cyclosporins and cyclosporine derivatives. The cyclosporine derivatives of the present invention are produced by chemical and isotopic substitution of the cyclosporine A (CsA) molecule by: (1) Chemical substitution and optionally deuterium substitution of amino acid 1; and (2) deuterium substitution at key sites of metabolism of the cyclosporine A molecule such as amino acids 1, 4, 9. Also disclosed are methods of producing the cyclosporine derivatives and method of producing immunosuppression with reduced toxicity with the disclosed cyclosporine derivatives.

9 Claims, 4 Drawing Sheets

U.S. PATENT DOCUMENTS

| | | | |
|---|---|---|---|
| 5,100,889 A | 3/1992 | Misra et al. | |
| 5,116,816 A | 5/1992 | Dreyfuss et al. | |
| 5,122,511 A | 6/1992 | Patchett et al. | |
| 5,129,884 A | 7/1992 | Dysarz | |
| 5,153,327 A | 10/1992 | Misra et al. | |
| 5,169,773 A | 12/1992 | Rosenthaler et al. | |
| 5,171,812 A | 12/1992 | Domb | |
| 5,190,935 A | 3/1993 | Binderup et al. | |
| 5,190,972 A | 3/1993 | Dumble | |
| 5,206,229 A | 4/1993 | Calverley et al. | |
| 5,214,130 A | 5/1993 | Patchett et al. | |
| 5,227,467 A | 7/1993 | Durette et al. | |
| 5,236,899 A | 8/1993 | Durette | |
| 5,239,057 A | 8/1993 | Wang et al. | |
| 5,256,547 A | 10/1993 | Rudat et al. | |
| 5,270,419 A | 12/1993 | Domb | |
| 5,284,826 A | 2/1994 | Eberle | |
| 5,298,523 A | 3/1994 | Longley et al. | |
| 5,318,901 A | 6/1994 | Patchett et al. | |
| 5,321,043 A | 6/1994 | Dumble | |
| 5,342,625 A | 8/1994 | Hauer et al. | |
| 5,350,574 A | 9/1994 | Erlanger et al. | |
| 5,356,633 A | 10/1994 | Woodle et al. | |
| 5,371,081 A | 12/1994 | Houghton et al. | |
| 5,382,655 A | 1/1995 | Szanya et al. | |
| 5,385,915 A | 1/1995 | Buxbaum et al. | |
| 5,389,382 A | 2/1995 | List et al. | |
| 5,393,669 A | 2/1995 | Brown | |
| 5,401,649 A | 3/1995 | Davalian et al. | |
| 5,401,731 A | 3/1995 | Calverley et al. | |
| 5,405,785 A | 4/1995 | Erlanger et al. | |
| 5,409,816 A | 4/1995 | Lundell et al. | |
| 5,411,952 A | 5/1995 | Kaswan | |
| 5,427,960 A | 6/1995 | Wang et al. | |
| 5,446,034 A | 8/1995 | Bretting et al. | |
| 5,447,924 A | 9/1995 | Bretting et al. | |
| 5,468,772 A | 11/1995 | Xu et al. | |
| 5,489,668 A | 2/1996 | Morrison et al. | |
| 5,498,421 A | 3/1996 | Grinstaff et al. | |
| 5,510,239 A | 4/1996 | Baracchini et al. | |
| 5,514,788 A | 5/1996 | Bennett et al. | |
| 5,525,590 A | 6/1996 | Bollinger et al. | |
| 5,527,820 A | 6/1996 | Ishizuka et al. | |
| 5,540,931 A | 7/1996 | Hewitt et al. | |
| 5,545,633 A | 8/1996 | Bretting | |
| 5,554,599 A | 9/1996 | Grue-S.o slashed.rensen et al. | |
| 5,554,725 A | 9/1996 | Pettit | |
| 5,571,799 A | 11/1996 | Tkachuk et al. | |
| 5,578,444 A | 11/1996 | Edwards et al. | |
| 5,589,458 A | 12/1996 | Jameson et al. | |
| 5,589,471 A | 12/1996 | Hansen et al. | |
| 5,591,623 A | 1/1997 | Bennett et al. | |
| 5,616,595 A | 4/1997 | Chu et al. | |
| 5,624,902 A | 4/1997 | Blondelle et al. | |
| 5,627,044 A | 5/1997 | Brown | |
| 5,632,991 A | 5/1997 | Gimbrone | |
| 5,635,207 A | 6/1997 | Grinstaff et al. | |
| 5,637,317 A | 6/1997 | Dietl | |
| 5,639,473 A | 6/1997 | Grinstaff et al. | |
| 5,639,724 A | 6/1997 | Cavanak | |
| 5,639,852 A | 6/1997 | Rich et al. | |
| 5,643,870 A | 7/1997 | Boelsterli et al. | |
| 5,648,376 A | 7/1997 | Strobel et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,665,543 A | 9/1997 | Foulkes et al. | |
| 5,667,764 A | 9/1997 | Kopia et al. | |
| 5,668,734 A | 9/1997 | Krishna et al. | |
| 5,670,478 A | 9/1997 | Stuchlik et al. | |
| 5,693,760 A | 12/1997 | Bringman et al. | |
| 5,698,448 A | 12/1997 | Soldin | |
| 5,709,797 A | 1/1998 | Bocchiola et al. | |
| 5,741,512 A | 4/1998 | Hauer et al. | |
| 5,741,775 A | 4/1998 | Balkovec et al. | |
| 5,747,330 A | 5/1998 | Casareto et al. | |
| 5,750,413 A | 5/1998 | Morrison et al. | |
| 5,750,678 A | 5/1998 | Bauer | |
| 5,756,706 A | 5/1998 | Mansour et al. | |
| 5,767,069 A | 6/1998 | Ko et al. | |
| 5,827,706 A | 10/1998 | Leitner et al. | |
| 5,834,266 A | 11/1998 | Crabtree et al. | |
| 5,840,305 A | 11/1998 | Bukrinsky et al. | |
| 5,871,753 A | 2/1999 | Belshaw et al. | |
| 6,605,593 B1 * | 8/2003 | Naicker et al. | 514/11 |
| 6,613,739 B1 * | 9/2003 | Naicker et al. | 514/11 |
| 6,998,385 B2 * | 2/2006 | Naicker et al. | 514/11 |
| 2005/0176628 A1 | 8/2005 | Naicker et al. | |
| 2006/0052290 A1 | 3/2006 | Naicker et al. | |

FOREIGN PATENT DOCUMENTS

| | | |
|---|---|---|
| CS | 8906498 | 9/1992 |
| DE | 3531597 | 3/1987 |
| DE | 3927804 | 3/1990 |
| DE | 4013910 | 10/1991 |
| DE | 4433101 | 3/1996 |
| DE | 19521974 | 12/1996 |
| DE | 19611094 | 9/1997 |
| EP | 0056782 | 8/1984 |
| EP | 0034567 | 11/1984 |
| EP | 0194972 | 9/1986 |
| EP | 0 283 801 A2 | 9/1988 |
| EP | 0294239 | 12/1988 |
| EP | 0296122 | 12/1988 |
| EP | 0300785 | 1/1989 |
| EP | 0321128 | 6/1989 |
| EP | 0 373 260 A1 | 6/1990 |
| EP | 0372541 | 6/1990 |
| EP | 0372862 | 6/1990 |
| EP | 0414632 | 2/1991 |
| EP | 0444897 | 9/1991 |
| EP | 0473961 | 3/1992 |
| EP | 0526200 | 2/1993 |
| EP | 0532187 | 3/1993 |
| EP | 0570829 | 11/1993 |
| EP | 0 557 544 A1 | 1/1994 |
| EP | 0 577 544 A1 | 1/1994 |
| EP | 0578616 | 1/1994 |
| EP | 0651995 | 5/1995 |
| EP | 0674178 | 9/1995 |
| EP | 0712631 | 5/1996 |
| FR | 2757520 | 6/1998 |
| FR | 2757521 | 6/1998 |
| FR | 2757522 | 6/1998 |
| GB | 2205317 | 12/1988 |
| GB | 2207678 | 2/1989 |
| GB | 2212499 | 7/1989 |
| GB | 2222770 | 3/1990 |
| GB | 2227244 | 7/1990 |
| GB | 2257359 | 1/1993 |
| GB | 2271121 | 4/1994 |
| GB | 2206119 | 12/1998 |
| JP | 52-061296 | 5/1977 |
| JP | 54-112840 | 9/1979 |
| JP | 57-163385 | 10/1982 |
| JP | 58-113161 | 7/1983 |
| JP | 1277755 | 11/1989 |
| JP | 2124100 | 5/1990 |
| JP | 02-184699 | 7/1990 |
| JP | 7178187 | 10/1995 |
| JP | 9048737 | 2/1997 |
| JP | 10029979 | 2/1998 |
| JP | 10251137 | 9/1998 |

| | | |
|---|---|---|
| JP | 63-258491 | 10/1998 |
| JP | 2001-519335 | 10/2001 |
| WO | WO 86/02080 | 4/1986 |
| WO | WO 90/00389 | 1/1990 |
| WO | WO 90/06763 | 6/1990 |
| WO | WO 92/04055 | 3/1992 |
| WO | WO 93/25533 | 12/1993 |
| WO | WO 95/05374 | 2/1994 |
| WO | WO 94/23733 | 10/1994 |
| WO | WO 94/25606 | 11/1994 |
| WO | WO 95/05372 | 2/1995 |
| WO | WO 95/11039 | 4/1995 |
| WO | WO 95/26325 | 10/1995 |
| WO | WO9526325 | 10/1995 |
| WO | WO 96/06857 | 3/1996 |
| WO | WO 96/22104 | 7/1996 |
| WO | WO 96/31202 | 10/1996 |
| WO | WO 96/33697 | 10/1996 |
| WO | WO 97/04005 | 2/1997 |
| WO | WO 97/25977 | 7/1997 |
| WO | WO 97/32541 | 9/1997 |
| WO | WO 97/33604 | 9/1997 |
| WO | WO 97/34639 | 9/1997 |
| WO | WO 98/08490 | 3/1998 |
| WO | WO 98/13066 | 4/1998 |
| WO | WO 98/14174 | 4/1998 |
| WO | WO 98/25590 | 6/1998 |
| WO | WO 98/46247 | 10/1998 |
| WO | WO 98/49193 | 11/1998 |
| WO | WO 99/10373 | 3/1999 |
| WO | WO 99/18120 | 4/1999 |

OTHER PUBLICATIONS

Park, S.B., et al. "A Semi-Synthetic Approach to Olefinic Analogs of Amino Acid One (MeBMT) in Cyclosporin A." *Tetrahedron Letters*, 30, 32, 4215-4218 (1989).

Patchett, A., et al. "Analogs of Cyclosporin A Modified at the D-ALA$^8$ Position." *J. Antibiotics*. 45(1): 94-102 (1992).

Seebach, D., et al. "Modification of Cyclosporin A (CS)[1]): Generation of an Enolate at the Sarcosine Residue and Reactions with Electrophiles." *Helvitica Chimica Acta*. 76 (1993).

Yohannes, D., et al. "Degredation of Rapamycin: Retrieval of Major Intact Subunits." *Tetrahedron Letters*. 33(49): 7469-7472 (1992).

von Wartberg, A., R. Traber. "Chemistry of the Natural Cyclosporin Metabolites." *Prog. Allergy*. 38 28-45 (1986).

von Traber, René, et al. "The Structure of Cyclosporin C." *Helvetica Chimica Acta* 60(4) 1247-1255 (1977).

Adams, M.W., "d-Alpha Tocopheryl Polyethylene Glycol 1000 Succinate (Eastman Vitamin E TPGS) as an Emulsifier and Bioenhancer for Drugs and Lipophilic Compounds", Pamphlet by Eastman Chemical Co., (Oct. 1996), pp. 254-262.

AEBI, Johannes D., et al., "Synthesis, Conformation, and Immunosuppressive Activities of Three Analouges of Cyclosporin A Modified in the 1-Position", *J. Med. Chem.*, vol. 33 (1990), pp. 99-1009.

Aspeslet, L, J. et al., "Requirements for Therapeutic Drug Monitoring of Sirolimus, an Immunosuppressive Agent Used in Renal Transplantation", Clinical Therapeutics, vol. 22 (2000), pp. B86-B92.

Barrett, A.G.M. et al., "B-[3-((Diisopropylamino)dimethylsil)allyl]diisopinocampheylborane: An Excellent Reagent for the Stereoselective Synthesis of Anti Vicinal Diols", *J Org Chem*, vol. 56 (1991), pp. 5243-5245.

Belshaw, P.J. et al., "Controlling protein association and subcellular localization with a synthetic ligand that induces heterodimerization of proteins", *Proceedings of the National Academy of Sciences of the USA*, vol. 93 (1996), pp. 4604-4607.

Bennet, W.M., "The Nephrotoxicity of New and Old Immunosuppressive Drugs", *Renal Failure*, vol. 20 (1998), pp. 687-690.

Bestmann, H.J., et al., "(Z)-5-Decenyl Accetate, A Sex Attractant for the Male Turnip Moth", *Agnew, Chem. Int. Ed. Engl.*, vol. 17, No. 10 (1978),pp. 768-769.

Biellmann, J.F., et al., "Allylic and Benzylic Carbanions Substituted by Heteroatoms", *Organic Reactions*, vol. 27 (1982), p. 9.

Blake, M. et al., "Studies with Deuterated Drugs", *Journal of Pharmaceutical* Sciences, vol. 64, No. 3 (Mar. 1975), pp. 367-391.

Borel, J.F. et al., "Biological Effects of Cyclosporin A: A New Antilymphocytic Agent", *Agents and Actions*, vol. 6 (1976), pp. 468-475.

Borel, J. F. et al., "Effects of the new anti-lymphocytic peptide cyclosporine A in Animals", *Immunology*, vol. 32, No. 6 (Jun. 1977), pp. 1017-1025.

Borok, Z., et al., "Effect of Glutathione Aerosol on Oxidant-Antioxidant Imbalance in Idiopathic Pulmonary Fibrosis", *The Lancet*, vol. 338 (Jul. 27, 1991), pp. 215 and 697.

Brown, H.C. et al., "Chrial Synthesis via Organobranes. 13, A Highly Diastereoselective and Enantioselective Addition of [(Z)-γ-Alkoxyallyl]diisopinocampheylboranes to Aldehydes" *J Am Chem Soc*, vol. 110 (1988), pp. 1535-1538.

Calne, R.Y. et al., "Cyclosporin A in a patients receiving renal allografts from cadaver donors", *The Lancet*, (Dec. 23 & 30, 1978) pp. 1323-1327.

Calne, R.Y. et al., "Pharmacological immunosuppression in clinical organ grafting. Observations on four agents: cyclosporine A. Asta 5122 (cytimun), lambada carrageenan and promethazine hydrochloride", *Clinical and Experimental Immunology*, vol. 35, No. 1 (Jan. 1979), pp. 1-9.

Carlsen, H.J. et al., "A Greatly Improved Procedure for Ruthenium Tetraoxide Catalyzed Oxidations of Organic Compounds", *J. Org. Chem.*, vol. 46, No. 19 (1981), pp. 3936-3938.

Carruthers, S.G. et al., "Simplified Liquid-Chromotographic Analysis for Cyclosporin A. and Comparison with Radioimmunoassay", *Clin Chem*, 29(1):180-183 (1983).

Chang, T., eta 1., "The Effect of Water-Soluble Vitamin E On Cyclosporine Pharmacokinetics in Healthy Volunteers", *Clin. Pharmacol. Ther.*, vol. 59 (1996), pp. 297-303.

Chen et al., "A sensitive enzyme immuoassay for Cyclosporin A using antibodies generated against a novel Hapten", *Research Communications in Molecular Pathology and Pharmacology*, vol, 88, No. 3 (Jun. 1995).

Christians et al., "Cyclosporine Metabolism in Transplant Patients", *Pharmac. Ther.*, vol. 57, pp. 291-345 (1993).

Copeland, K.R. et al., "Toxicity of Cyclosporine Metabolites", *Ther Drug Monit*, 12(6):525-532 (Nov. 1990).

Corey, E.J., et al., "Highly Reactive Equivalents of Allylindenetriphennylphosporanes For the Stereospecific Synthesis of 1,3-dienes by Cis-Olefination of Hindered Aldehydes", *Tetrahedron Letters*, vol. 26, No. 47 (1985), pp. 5747-5748.

Dreyfuss, M. et al., "Cyclosporin A and C", *European Journal of Applied Microbiology*, vol. 3 (1976), pp. 125-133.

Eberle, M.K., et al., "Synthesis of the Main Metabolite (OL-17) of Cyclosporin A ", *J. Org. Chem.*, vol. 57 (1992), pp. 2689-2691.

Eberle, Marcel K., et al., "Modifications of the MeBmt Side Chain of Cyclosporin A", *Biorganic & Medicinal Letters*, vol. 5, No. 15 (1995), pp. 1725-1728.

Ehlinger, E., et al., "Silicon in Synthesis. 10. The (trimethylsily)allyl amion: A β-acyl anion Equivalent for the conversion of Aldehydes and Ketones into γ-Lactones", *J. Am. Chem. Soc.*, vol. 102, No. 15 (1980), pp. 5004-5011.

Etzkorn, F. et al., "Cyclophilin Residues That Affect noncompetitive Inhibition of the Protein Serine Phosphatase Activity of Calcineurin by the Cyclophilin-Cyclosporin A Complex", *Biochemistry*, vol. 33 (1994), pp. 2380-2388.

Foster, A. B. et al., "Deuterium Isotope Effects in the Metabolism of Drugs and Xenbiotics: Implications for Drug Design", *Advances in Drug Research*, Academic Press, London, vol. 14 (1985), pp. 2-40.

Fruman, D.S., et al., "Calcineurin Phosphatase Activity in T Lymphocytes Is Inhibited by FK 506 and Cyclosporin A", *Proc. Natl. Acad. Sci. USA*, vol. 89 (1992), pp. 3686-3690.

Gordon, M.Y. et al., "Selective effects of cyclosporine A on colony-forming lymphoid and myeloid cells in man", *Nature*, vol. 279 (May 31, 1979), pp. 434-434.

Granelli-Piperno, A., et al., "Lymphokine and Nonlymphokine mRNA Levels in Stimulated Human T Cells: Kinetics, Mitogen Requirements, and Effects of Cyclosporin A", *J. Exp. Med.*, vol. 163 (1986), p.922-937.
Harlow et al., "Antibodies, A Laboratory Manual", *Cold String Harbor Laboratory* , New York (1988).
Hartman, N.R. et al., "Mass Spectrometric Analysis of Cyclosproine Metabolites", *biomed. Environ. Mass Spectrum.*, vol. 13 (1986), pp. 361-372.
Hebert, M.F. et al., "Bioavailabity of cyclosporine with Concomitant Rifampin Administration is Markedly Less than Predicted by Hepatic Enzyme Induction", *Clin. Pharmacol. Ther.*, vol. 52 (1992), pp. 453-457.
Hoffman, R.W., et al., "Diastereoselective Addition of γ-Alkylthio-Allylboronates to Aldehydes", *Tetrahedron Letters*, vol. 21 (1980), pp. 4883-4886.
Hoffman, R.W., et al., "Stereoselective Synthesis of Alcohols. 8. Diastereoselective Synthesis of β-methyllomoallyl Alcohols via Crotylboronates", *J. Org. Chem.*, vol. 46 (1981), pp. 1309-1314.
Höfle, G., et al., "4-Dialkylaminopyrides as Highly Active Acylation Catalysts", *Agnew. Chem. Int. Ed. Engl.*, vol. 17 (1978), pp. 569-583.
Holt, D. et al., "Cyclosporin and vitamin E", *The Lancet*, vol. 338 (Sep. 14, 1991), pp. 697.
Hon et al., "A convenient and efficient workup of ozonolysis reactions using triethylamine", *Synthetic Communications*, vol. 23, No. 11 (1993), pp. 1543-1553.
House, H.O., *Modern Synthetic Reactions* (W.A. Benjamin, Menlo Park, California, 2nd ed., 1972), pp. 302-319.
Hu, S. et al., "Diastereoselective Chloroallylboration of α-Chiral Aldehydes", *J Org Chem*, vol. 63 (1998), pp. 8843-8849.
Hurdrlik, P.F., et al., "Stereospecific Olefin-Forming Elimination Reactions of β-Hydroxyalkylsilanes", *J. Am. Chem., Soc.*, vol. 97, No. 6 (1975), pp. 1464-1468.
Ikeda, Y., et al., "Stereoselective Synthesis of (Z)- and (E)-1,3-alkadienes from Aldehydes Using Organotitanium and Lithium Reagents", *Tetrahedron*, vol. 43, No. 4 (1987), pp. 723-730.
Johnson et al., "The Chemistry of Ylids--V Trialkylphosphoniumfluorenylides Mechanism of the Wittig Reaction", *Tetrahedon*, vol. 9 (1960), pp. 130-139.
Johnson, R.A. et al., *Catalytic Asymmetric Synthesis*, Edited by I. Ojima, VCH Publishers, New York, (1993), pp. 103-158.
Kobel, H. et al., "Contribution to knowledge of the biosynthesis of cyclosporin A", Birkhauser Verlag Basel, *Experientia*, vol. 39 (1983), pp. 873-876.
Kobel et al., "Directed Biosynthesis of Cyclosporins", *EP. J. Applied Microbiology and Biotechnology*, vol. 14 (1982), pp. 237-240.
Lawen, A. et al., "Cell-free biosynthesis of new cyclosporins", *The Journal of Antibiotics*, vol. 42, No. 8 (Aug. 1989), pp. 1283-1289.
Liu, J. et al., "Calcineurin Is a Common Target of Cyclophilin-Cyclosporin A and FKBP-FK506 Complexes", *Cell*, vol. 66 (Aug. 23, 1991), pp. 807-815.
Marshall, J.A., "Chiral Allylic and Allenic Stannanes as Reagents for Asymmetric Synthesis", *Chemical Reviews*, vol. 96 (1996), pp. 31-47.
Metelitsa, D.I., "Reaction Mechanisms of the Direct Epoxidation of Aldenes in the Liquid Phase", *Russian Chemical Reviews*, vol. 41, No. 10 (Oct. 1972), pp. 807-821.
Petcher, T.J. et al., "Chrystal and Molecular Structure of an Iodo-derivative of the Cyclic Undecapeptide Cyclosporin A", *Helvetica Chimica Acta*, vol. 50, Fasc. 5 (1976), pp. 1480-1488.
Peterson, D., "A Carbonyl Olefination Reaction Using Silyl-Substituted Organometallic Compounds", *J. Org. Chem.*, vol. 33 (1967), pp. 780-784.
Pflugl, G. et al., "X-ray structure of a decameric cyclophilin-cyclosporin crystal complex" *Nature*, vol. 361 (Jan. 7, 1993), pp. 91-94.
Prileschajew, N. "Oxydation ungesättigter Verbindungen mittels organischer Superoxyde", *Berichte der Deutschen Chemischen Gesellschaft*, (1909), pp. 4811-4815, English translation attached.
Reetz, M.T., *Organotitanium Reagents in Organic Synthesis*, (1986-Springer-Verlag, Berlin), pp. VII, 148-149 and 162-168.
Rich, D., et al., "Synthesis and Antimitogenic Activities of Four Analogues of Cyclosporin A Modified in the 1-Position", *J. Med. Chem.*, vol. 29 (1988), p. 978-984.
Roush, W.R., "1.1 Allyl Organometallics", *Comp. Org Synth.*, vol. 2, No. 1(1991), pp. 1-53.
Rüegger, A. et al., "Cyclosporin A, ein immunsuppressiv wirksamer Peptidmetabolit aus *Trichoderma polysporum* (Link Ex Pers.) *Rifai", Helvetica Chimica Acta*, vol. 59, Fasc 4. (1976), pp. 1075-1092, English translation attached.
Schnurpfeil, D., *Zur Kataylse der Prilesaev-Reaktion*, vol. 20 (1980, p. 445, English translation attached.
Schrieber, S.F., et al., "The Mechanism of Action of Cyclosporin A and FK506", *Immunol. Today*, vol. 13 (1992), pp. 136-142.
Seebach, D. et al., "Modification of Cyclosporin A (CS)[1] ): Generation of an Enolate at the Sarcosine Residue and Reactions with Electrophiles", *Helvitica Chimica Acta*, vol. 76 (1993), pp. 1564-1590.
Sharpless, K.B. et al., "The Osmium-Catalyzed Asymmetric Dihydroxylation: A New Ligand Class and a Process Improvement", *J Org Chem*, vol. 57, No. 10 (1992), pp. 2768-2771.
Sketris, I., et al., "Optimizing the Use of Cyclosporine in Renal Transplatation", *Clin. Biochem.*, vol. 28 (1995), pp. 195-211.
Sokol, R. et al, "Improvement of Cyclosporin absorption in children after liver transplantation by means of water-soluble vitamin E", *The Lancet*, vol. 338 (Jul. 27, 1991), pp. 212-214.
Streitwieser, Jr., A., et al., "16.4 Protecting Groups" and 27.3 "Preparation of Diols", *Intro To Org. Chem.*, 2$^{nd}$ Ed., McMillan Publishing Co., Inc., New York, NY (1981), pp. 475-476 and 844-846, respectively.
Swern, D., "Chapter 7: Epoxidation and Hydroxylation of Ethylenic Compounds with Organic Peracids", *Organic Reactions*, vol. 7 (1953), pp. 378-433.
Swern, D., "Organic Peracids", *Chemical Review*, vol. 45 (1949), p. 16.
Tamura et al., "Stereoselective E and Z Olefin Formatino by Wittig Olefination of Aldehydes with Allylic Phosphorus Hlides. Stereochemistry". *J Org Chem*, vol. 53 (1988), pp. 2723-2728.
Thliveris, J.A., et al., "Chronic Ciclosporin Nephrotoxicity: A Rabit Model", *Nephron*, vol. 57 (1991), pp. 470-476.
Thliveris, J.A., et al., "Chronic Cyclosporine-Induced Nephrotoxcity: A Rabbit Model", *Transplantation*, vol. 57 (1994), pp. 774-776.
Thomas, S.E., *Organic Synthesis: the Roles of Boron and Silicon*, Oxford University Press, New York, NY, (1991), pp. 34-35, 67-69 and 85-87.
Traber, R, et al., "162. Isolierung und Strukturermittlung der neuen Cyclosporine E,F,G, H and I", *Helv. Chim. Acta*, vol. 65 (1982), pp. 1655-1677 (1982), summary in English.
Traber, R. et al., "Cyclosporins-New Analogues by Precursor Directed Biosynthesis", *The Journal of Antobiotics*, vol. 42, No. 4 (Apr. 1989), pp. 591-597.
Traber, R. et al., "Neue Cyclosporine aus *Tolypocladium inflatum* Die Cyclosporine K-Z", *Helvetica Chimica Acta*, vol. 70 (1987), pp. 13-36, English translation attached.
Tsai, D.J.S., et al., "A Sterocontrolled Synthesis of (*Z* ) and (*E* ) Terminla Dienes from Pinacol (*E* )-1-Trimethylsiyl-1-Propene-3-Boronate", *Tetrahedron Letters* , vol. 22, No. 29 (1981), pp. 2751-2752.
Tutschka, P.J. et al., "Cyclosporin-A to Prevent Graft-Versus-Host Disease: A Pilot Study in 22 Patients Receiving Allogeneic Marrow Transplants", *Blood*, vol. 61, No. 2 (Feb. 1983), pp. 318-325.
Ukai, J., et al., "Direct, Stereoselective Synthesis of Ehter *E* - or - *Z* -1, 3-Dienes", *Tetrahedron Letters*, vol. 24, No. 37 (1983), pp. 4029-4032.
Valentine, H.A., et al., "Recent Advances in Cardiac Transplantation", *N. Eng. J. Med.*, [editorial comment], vol. 333, No. 10(1995), pp. 660-661.
Von Wartburg, A. et al., "Cyclosporins, Fungal Metabolites with Immunosuppressive Activities", *Progress in Medicinal Chemistry 25*, (1998), pp. 1-33.
Wang, et al., "Cyclosporine Nephrotoxicity: Attenuation By an Antioxiodiant-Inhibitor of Lipid Peroxidation In Vitro and In Vivo", *Transplantation*, vol. 58 (1994), pp. 940-946.

Weidmann, B., et al., “Organometallic Compounds of Titanium and Zirconium as Selective Neucleophilic Reagents in Organic Synthesis”, *Agnes. Chem. Int. Ed. Engl.*, vol. 22 (1983), pp. 34-45.
Wenger, R., “Cyclosporine and Analogues-Isolation and Synthesis - Mechanism of Action and Structural Requirements for Pharmacological Activity”, *Progress in the Chemistry of Organic Natural Products*, vol. 50 (1986), pp. 123-168.
Wenger, R. “Synthesis of Cyclosporine and Analogues: Structural Requirements for Immunosuppresive Activity”, *Agnew. Chem. Int. Ed.*, vol. 24 (1985), pp. 77-85.
Wenger, R., “Synthesis of Cyclosporine and Analouges: Structure, Activity, Relationships of New Cyclosporine Derivatives”, *Transpl. Proc.*, vol. 15, Supp. 1 (1983), pp. 2230-2241.
White, D.J.G. et al., “Cyclosporin A: An Immunosuppressive Agent Prefentially Active Against Proliferating T Cells ”, *Transplantation*, vol. 27, No. 1 (1979), pp. 55-58.
Yamamoto, Y., et al., “Selective Reactions Using Allylic Metals”, *Chemical Reviews*, vol. 93 (1993), pp. 2207-2293.
Yang, D. et al., “A $C_2$Symmetric Chiral Ketone for Catalytic Aysmmetric Epoxidation of Unfunctionalized Olefins”, *J. Am. Chem. Soc.*, vol. 118 (1996), pp. 491-492.
Yang, D., et al., “Novel Cyclic Ketones for Catalytic Oxidation Reactions”, *J. Org. Chem.*, vol. 63 (1998), pp. 9888-9894.

* cited by examiner

DEUTERATED CYCLOSPORINE ANALOGS AND METHODS OF MAKING THE SAME

CROSS-REFERENCE TO RELATED APPLICATIONS

This application is a continuation of U.S. application Ser. No. 10/319,835, filed Dec. 16, 2002 now abandoned, which is a continuation of U.S. application Ser. No. 09/634,945, filed Aug. 7, 2000, now U.S. Pat. No. 6,613,739, which is a continuation of U.S. application Ser. No. 09/184,109, filed Nov. 2, 1998, now abandoned which is a continuation under 35 U.S.C. §120 of International Patent Application Serial No. PCT/IB98/01693, filed Oct. 8, 1998, which claims benefit of U.S. Provisional Application No. 60/061,360 filed Oct. 8, 1997. The disclosure of each of the above applications is incorporated herein by reference in its entirety.

INTRODUCTION AND BACKGROUND

Cyclosporin derivatives of the present invention are disclosed which possess enhanced efficacy and reduced toxicity over naturally occurring and other presently known cyclosporins and cyclosporine derivatives. The cyclosporin derivatives of the present invention are produced by chemical and isotopic substitution of the cyclosporine A (CsA) molecule by:

1. Chemical substitution and optionally deuterium substitution of amino acid 1; and
2. Deuterium substitution at key sites of metabolism of the cyclosporine A molecule such as amino acids 1, 4, 9.

The cyclosporins are a family of, neutral, hydrophobic cyclic undecapeptides, containing a novel nine-carbon amino acid (MeBmt) at position 1 of the ring that exhibit potent immunosuppressive, antiparasitic, fungicidal, and chronic anti-inflammatory properties. The naturally occurring members of this family of structurally related compounds are produced by various fungi imperfecti. Cyclosporines A and C, are the major components. Cyclosporine A, which is discussed further below, is a particularly important member of the cyclosporin family of compounds. Twenty four minor metabolites, also oligopeptides, have been identified: Lawen et al, J. Antibiotics 42, 1283 (1989); Traber et al, Helv. Chim. Acta 70, 13 (1987); Von Wartburg and Traber Prog. Med. Chem., 25, 1 (1988).

Isolation of cyclosporines A and C, as well as the structure of A were reported by A. Ruegger et al., Helv. Chim. Acta 59, 1075 (1976); M. Dreyfuss et al., J. Appl. Microbiol. 3, 125 (1976). Crystal and molecular structures of the iodo derivative of A have been reported by T. J. Petcher et al., Helv. Chim. Acta 59, 1480 (1976). The structure of C was reported by R. Traber et al., ibid. 60, 1247 (1977). Production of A and C has been reported by E. Harri et al., U.S. Pat. No. 4,117,118 (1978 to Sandoz). Isolation, characterization and antifungal activity of B, D, E, as well as the structures of A through D have been reported by R. Traber et al., Helv. Chim. Acta 60, 1568 (1977). Isolation and structures of E, F, G, H, I: eidem, ibid. 65, 1655 (1982). Preparation of [2-Deutero-3-fluoro-D-Ala]$^8$-CsA is disclosed by Patchett et al in GB 2,206,199A which was published on Dec. 29, 1988.

Cyclosporin was discovered to be immunosuppressive when it was observed to suppress antibody production in mice during the screening of fungal extracts. Specifically, its suppressive effects appear to be related to the inhibition of T-cell receptor-mediated activation events. It accomplishes this by interrupting calcium dependent signal transduction during T-cell activation by inactivating calmodulin and cyclophilin, a peptidyl propyl isomerase. It also inhibits lymphokine production by T-helper cells in vitro and arrests the development of mature CD8 and CD4 cells in the thymus. Other in vitro properties include inhibition of IL-2 producing T-lymphocytes and cytotoxic T-lymphocytes, inhibition of IL-2 released by activated T-cells, inhibition of resting T-lymphocytes in response to alloantigen and exogenous lymphokine, inhibition of IL-1 production, and inhibition of mitogen activation of IL-2 producing T-lymphocytes. Further evidence indicates that the above effects involve the T-lymphocytes at the activation and maturation stages.

Stimulation of TCR (T cell receptor) by foreign antigen on a major histocompatibility (MHC) molecule on the surface of the T cell results in the activation of a TCR signal transmission pathway (exact method of transmission unknown) through the cytoplasm causing the signal results in the activation of nuclear transcription factors, i.e. nuclear factors of activated T-cells (NF-AT) which regulate transcription of T-cell activation genes. These genes include that of lymphokine interleukin-2 (IL-2). Translation of the message is followed by secretion of IL-2. T-cell activation also involves the appearance of the lymphokine receptor IL-2R on the cell surface. After IL-2 binds to IL-2R, a lymphokine receptor (LKR) signal transmission pathway is activated. The immunosuppressive drug, rapamycin, inhibits this pathway.

CsA is a potent inhibitor of TCR-mediated signal transduction pathway. It inhibits binding of NF-AT to the IL-2 enhancer, and thus inhibits transcriptional activation. CsA binds to cyclophilin, which binds to calcineurin, which is a key enzyme in the T-cell signal transduction cascade.

Cyclophilin is found in prokaryotic and eukarotic organisms and is ubiquitous and abundant. Cyclophilin is a single polypeptide chain with 165 amino acid residues. It has a molecular mass of 17.8 kD. A roughly spherical molecule with a radius of 17 angstroms, cyclophilin has an eight-stranded antiparallel beta barrel. Inside the barrel, the tightly packed core contains mostly hydrophobic side chains. CsA has numerous hydrophobic side chains which allow it to fit into the cyclophilin beta barrel. Cyclophillin catalyzes the interconversion of the cis and trans-rotamers of the peGIFdyl-prolyl amide bond of peptide and protein substrates. Cyclophilin is identical in structure with peptidyl prolyl cis-trans isomerase and bears structural resemblance to the superfamily of proteins that transports ligands such as retinol-binding protein (RBP). These proteins carry the ligand in the barrel core. But cyclophilin actually carries the ligand binding site on the outside of the barrel. The tetrapeptide ligand binds in a long deep groove on the protein surface between one face of the beta barrel and the Thr116-Gly130 loop.

Further properties have also been reported in studies of the biological activity of CsA: J. F. Borel et al., Agents Actions 6, 468 (1976). Pharmacology: Eidem. Immunology 32, 1017 (1977); R. Y. Calne, Clin. Exp. Immunol. 35, 1 (1979). Human studies: R. Y. Calne et al., Lancet 2, 1323 (1978); R. L. Powles et al., ibid. 1327; R. L. Powles et al., ibid 1, 327 (1980). In vitro activity (porcine T-cells): D. J. White et al., Transplantation 27, 55 (1979). Effects on human lymphoid and myeloid cells: M. Y. Gordon, J. W. Singer, Nature 279, 433 (1979). Clinical study of CsA in graft-versus-host disease: P. J. Tutschka et al., Blood 61, 318 (1983).

Mechanism of Cyclosporine A Action

Cyclosporine A-Cyclophilin A Complex

CsA, as discussed above, binds to the cyclophilin beta barrel. Thirteen CyP A residues define the CsA binding site. These residues are Arg 55, Phe 60, Met 61, Gln 63, Gly 72, Ala 101, Asn 102, Ala 103, Gln 111, Phe 113, Trp 121, Leu 122, His 126. The largest side-chain movements are 1.3 A for Arg 55 and up to 0.7 A for Phe 60, Gln 63, and Trp 121. There are four direct hydrogen bonds between the CyP A and CsA. Residues 4, 5, 6, 7, 8 of CsA protrude out into the solvent and are thought to be involved in binding the effector protein, calcineurin (Pflugl, G., Kallen, J., Schirmer, T., Jansonius, J. N., Zurini, M. G. M., & Walkinshaw, M. D. (1993) Nature 361, 91-94.)

Function of CsA-CyP A Complex

The CsA-CyP A complex inhibits the phosphatase activity of the heterodimeric protein serine/threonine phosphatase or calcineurin (Liu, J., Farmer, J. D., Lane, W. S., Friedman, J., Weissman, I., & Schreiber, S. L. (1991) Cell 66, 807-15.; Swanson, S. K., Born, T., Zydowsky, C. D., Cho, H., Chang, H. Y., & Walsh, C. T. (1992) Proc. Natl. Acad. Sci. USA 89, 3686-90). CyP A binds CsA with an affinity of ca. 10 nM. The complex is then presented to calcineurin (Liu, J., Farmer, J. D., Lane, W. S., Friedman, J., Weissman, I., & Schreiber, S. L. (1991) Cell 66, 807-15.).

Calcineurin dephosphorylates the transcription factor NFAT found in the cytoplasm of T-cells. Dephosphorylation allows NFAT to translocate to the nucleus, combine with jun/fos genes and activate the transcription of the IL-2 gene responsible for cell cycle progression, leading to immune response. CsA-CyP A complex inhibits the phosphatase activity of calcineurin and ultimately immunosuppression (Etzkorn, F. A., Chang, Z., Stolz, L. A., & Walsh, C. T. (1994) Biochemistry 33, 2380-2388.). Neither CsA or CyP A alone are important immunologically. Only their complex is important (Liu, J., Farmer, J. D., Lane, W. S., Friedman, J., Weissman, I., & Schreiber, S. L. (1991) Cell 66, 807-15).

Metabolism of Cyclosporine:

Cyclosporine is metabolized in liver, small intestine and kidney to more than 30 metabolites. The structure of 13 metabolites and 2 phase II metabolites have been identified and at least 23 further metabolites have been isolated by HPLC and their structures characterized by mass spectrometry. The reactions involved in phase I metabolism of cyclosporine are hydroxylation, demethylation as well as oxidation and cyclisation at amino acid 1. Several clinical studies and reports showed an association between blood concentrations of cyclosporine metabolites and neuro- or nephrotoxicity. In vitro experiments indicate that metabolites are considerably less immunosupressive and more toxic than CsA.

As exemplified by the ever expanding list of indications for which CsA has been found useful, the cyclosporin family of compounds find utility in the prevention of rejection or organ and bone marrow transplants; and in the treatment of psoriasis, and a number of autoimmune disorders such as type 1 diabetes mellitus, multiple sclerosis, autoimmune uveitis, and rheumatoid arthritis. Additional indications are discussed infra.

As is generally accepted by those of skill in the art, inhibition of secretion of interleukin-2 (IL-2) and other lymphokines from lymphocytes, is a useful indicator of intrinsic immunosuppressive activity of a cyclosporin analog. For a recent review of cyclosporin uses and mechanisms of action see Wenger et al Cyclosporine: Chemistry, Structure-Activity Relationships and Mode of Action, Progress in Clinical Biochemistry and Medicine, vol. 2, 176 (1986).

Cyclosporin A is a cyclic peptide which contains several N-methyl amino acids and, at position-8, contains a D-alanine. The structure of Cyclosporin A[a] is given below:

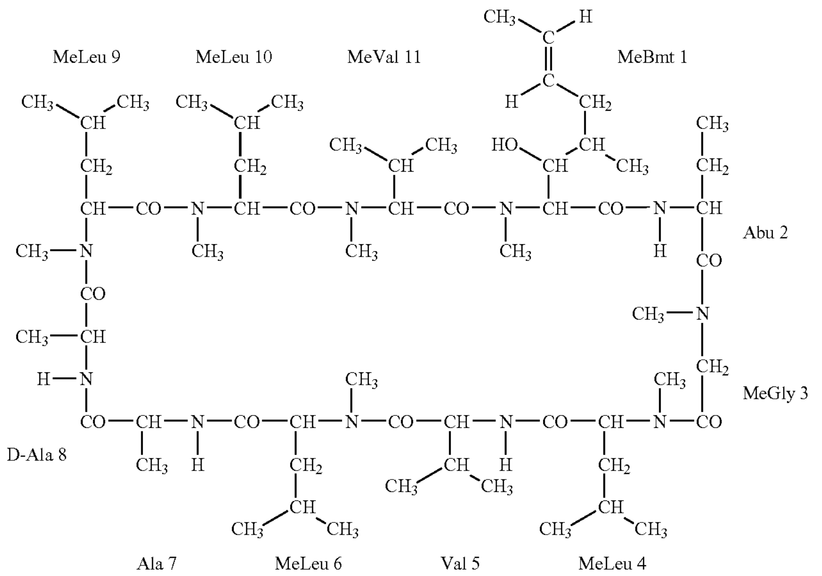

[a]Unless otherwise specified, each of the amino acids of the disclosed cyclosporin is of the L-configuration.

As is the practice in the field, a particular cyclosporin analog may be named using a shorthand notation identifying how the analog differs from cyclosporin A. Thus, cyclosporin C which differs from cyclosporin A by the threonine at position-2 may be identified as $[Thr]^2$-cyclosporin or $[Thr]^2$-CsA. Similarly, cyclosporin B is $[Ala]^2$-CsA; cyclosporin D is $[Val]^2$-CsA; cyclosporin E is $[Val]^{11}$-CsA; cyclosporin F is $[3\text{-DesoxyMeBmt}]^1$-CsA; cyclosporin G is $[NVa]^2$-CsA; and cyclosporin H is $[D\text{-MeVal}]^{11}$-CsA.

D-Serine and D-Threonine have been introduced into the 8-position of cyclosporin A by biosynthesis resulting in active compounds. See R. Traber et al. *J. Antibiotics* 42, 591 (1989). D-Chloroalanine has also been introduced into position-8 of Cyclosporin A by biosynthesis. See A. Lawen et al *J. Antibiotics* 52, 1283 (1989).

Indications for Cyclosporine Therapy

Immunoregulatory abnormalities have been shown to exist in a wide variety of autoimmune and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents, such as NSAID's (Non-Steroidal Anti-inflammatory Drugs), and corticosteroids act principally by blocking the effect of, or secretion of, these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Generally, a cyclosporin, such as cyclosporine A, is not cytotoxic nor myelotoxic. It does not inhibit migration of monocytes nor does it inhibit granulocytes and macrophage action. Its action is specific and leaves most established immune responses intact. However, it is nephrotoxic and is known to cause the following undesirable side effects:

(1) abnormal liver function;
(2) hirsutism;
(3) gum hypertrophy;
(4) tremor;
(5) neurotoxicity;
(6) hyperaesthesia; and
(7) gastrointestinal discomfort.

A number of cyclosporines and analogs have been described in the patent literature:

U.S. Pat. No. 4,108,985 issued to Ruegger, et al. on Aug. 22, 1978 entitled, "Dihydrocyclosporin C", discloses dihydrocyclosporin C, which can be produced by hydrogenation of cyclosporin C.

U.S. Pat. No. 4,117,118 issued to Harri, et al. on Sep. 26, 1978 entitled, "Organic Compounds", discloses cyclosporins A and B, and the production thereof by fermentation.

U.S. Pat. No. 4,210,581 issued to Ruegger, et al. on Jul. 1, 1980 entitled, "Organic Compounds", discloses cyclosporin C and dihydrocyclosporin C which can be produced by hydrogenation of cyclosporin C.

U.S. Pat. No. 4,220,641, issued to Traber, et al. on Sep. 2, 1980 entitled, "Organic Compounds", discloses cyclosporin D, dihydrocyclosporin D, and isocyclosporin D.

U.S. Pat. No. 4,288,431 issued to Traber, et al. on Sep. 8, 1981 entitled, "Cyclosporin Derivatives, Their Production and Pharmaceutical Compositions Containing Them", discloses cyclosporin G, dihydrocylosporin G, and isocyclosporin G.

U.S. Pat. No. 4,289,851, issued to Traber, et al. on Sep. 15, 1981 entitled, "Process for Producing Cyclosporin Derivatives", discloses cyclosporin D, dihydrocyclosporin D, and isocyclosporin D, and a process for producing same.

U.S. Pat. No. 4,384,996, issued to Bollinger, et al. on May 24, 1983 entitled "Novel Cyclosporins", discloses cyclosporins having a β-vinylene-α-amino acid residue at the 2-position and/or a β-hydroxy-α-amino acid residue at the 8-position. The cyclosporins disclosed included either MeBmt or dihydro-MeBmt at the 1-position.

U.S. Pat. No. 4,396,542, issued to Wenger on Aug. 2, 1983 entitled, "Method for the Total Synthesis of Cyclosporins, Novel Cyclosporins and Novel Intermediates and Methods for their Production", discloses the synthesis of cyclosporins, wherein the residue at the 1-position is either MeBmt, dihydro-MeBmt, and protected intermediates.

U.S. Pat. No. 4,639,434, issued to Wenger, et al on Jan. 27, 1987, entitled "Novel Cyclosporins", discloses cyclosporins with substituted residues at positions 1, 2, 5 and 8.

U.S. Pat. No. 4,681,754, issued to Siegel on Jul. 21, 1987 entitled, "Counteracting Cyclosporin Organ Toxicity", discloses methods of use of cyclosporin comprising co-dergocrine.

U.S. Pat. No. 4,703,033 issued to Seebach on Oct. 27, 1987 entitled, "Novel Cyclosporins", discloses cyclosporins with substituted residues at positions 1, 2 and 3. The substitutions at position-3 include halogen.

H. Kobel and R Traber, *Directed Biosynthesis of Cyclosporins*, European J. Appln. Microbiol Biotechnol., 14, 237B240 (1982), discloses the biosynthesis of cyclosporins A, B, C, D & G by fermentation.

Additional cyclosporin analogs are disclosed in U.S. Pat. No. 4,798,823, issued to Witzel, entitled, New Cyclosporin Analogs with Modified "C-9 amino acids", which discloses cyclosporin analogs with sulfur-containing amino acids at position-1.

SUMMARY OF THE INVENTION

The present invention concerns chemically substituted and deuterated analogs of cyclosporine A and related cyclosporines.

An object of the present invention is to provide new cyclosporine analogs which have enhanced efficacy and altered pharmacokinetic and pharmacodynamic parameters. Another object of the present invention is to provide a cyclosporine analog for the care of immunonoregulatory disorders and diseases, including the prevention, control and treatment thereof. An additional object of the present invention is to provide pharmaceutical compositions for administering to a patient in need of the treatment one or more of the active immunosuppressive agents of the present invention. Still a further object of this invention is to provide a method of controlling graft rejection, autoimmune and chronic inflammatory diseases by administering a sufficient amount of one or more of the novel immunosuppressive agents in a mammalian species in need of such treatment. Finally, it is the object of this invention to provide processes for the preparation of the active compounds of the present invention.

Substitution and deuteration of the cyclosporine molecule results in altered physicochemical and pharmacokinetic properties which enhance its usefulness in the treatment of transplantation rejection, host vs. graft disease, graft vs. host disease, aplastic anemia, focal and segmental glomerulosclerosis, myasthenia gravis, psoriatic arthritis, relapsing polychondritis and ulcerative colitis.

Embodiments of the invention include CsA derivatives wherein one or more hydrogen atoms in the 1, 3 and 9 amino acid positions can be substituted with a deuterium atom and wherein the cyclosporine A derivatives are optionally chemically substituted at the amino acid 9 position. A further specific embodiment of the invention is the CsA derivative represented by formula I:

(I)

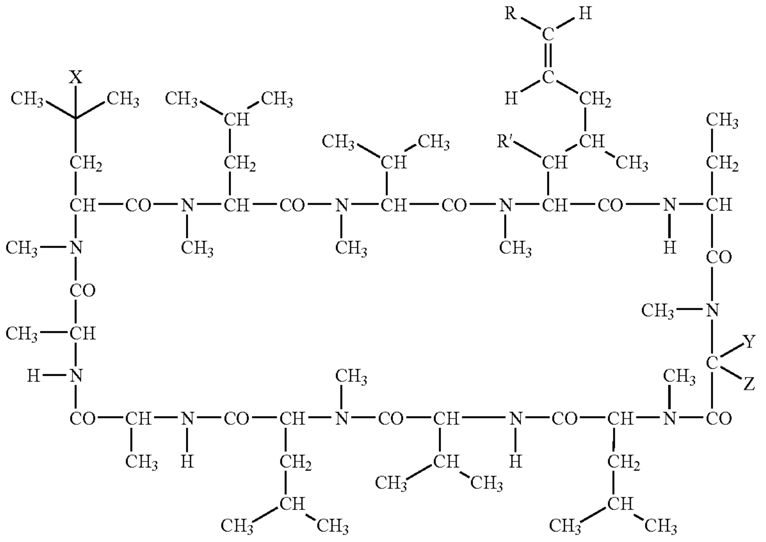

where R is (i) a deuterium or (ii) a saturated or unsaturated straight or branched aliphatic chain of from 2 to 16 carbon atoms and optionally containing one or more deuterium atoms or an ester, ketone or alcohol of the carbon chain and optionally containing one or more substituents selected from halogen, nitro, amino, amido, aromatic, and heterocyclic, or (iii) R is an aromatic or heterocyclic group optionally containing a deuterium atom, or (iv) R is a methyl group and X, Y, and Z are hydrogen or deuterium provided that at least one of X, Y or Z is deuterium and R' is an OH or an ester or is an O and together with a carbon adjacent to a double bond on amino acid 1 form a heterocyclic ring such as 5-membered rings where the heteroatom is oxygen. Other specific embodiments of the present invention include the CsA derivative of formula I where R is a saturated or unsaturated carbon chain of from 2 to 3 carbons containing one or more deuterium. Further specific embodiments include those of formulas 5g and 5e below:

(5g)

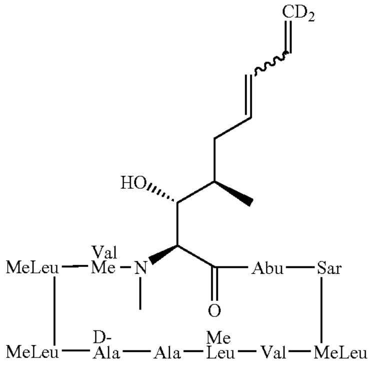

-continued (5e)

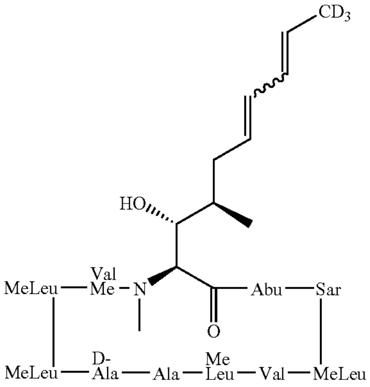

DETAILED DESCRIPTION OF THE INVENTION

Figure 1:
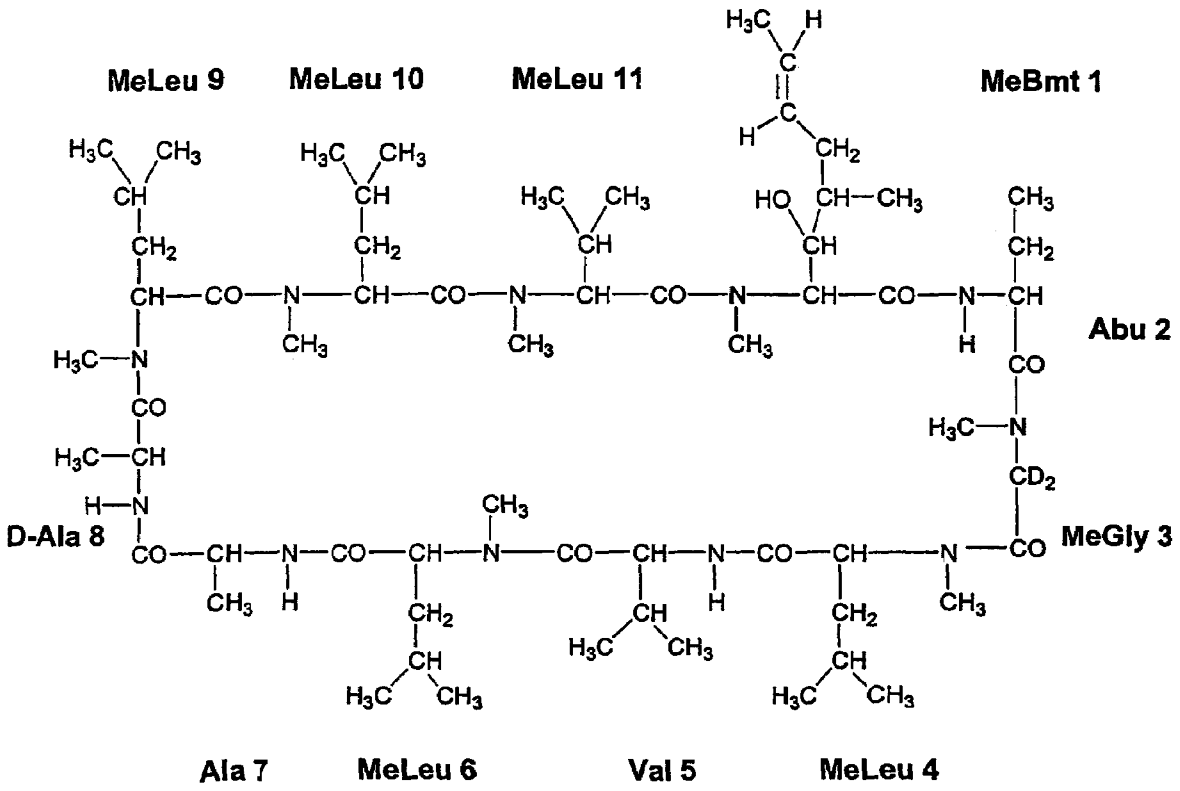
FIG. 1 is the structure of cyclosporine A showing a site of deuteration at the amino acid 3 position.
Figure 2:
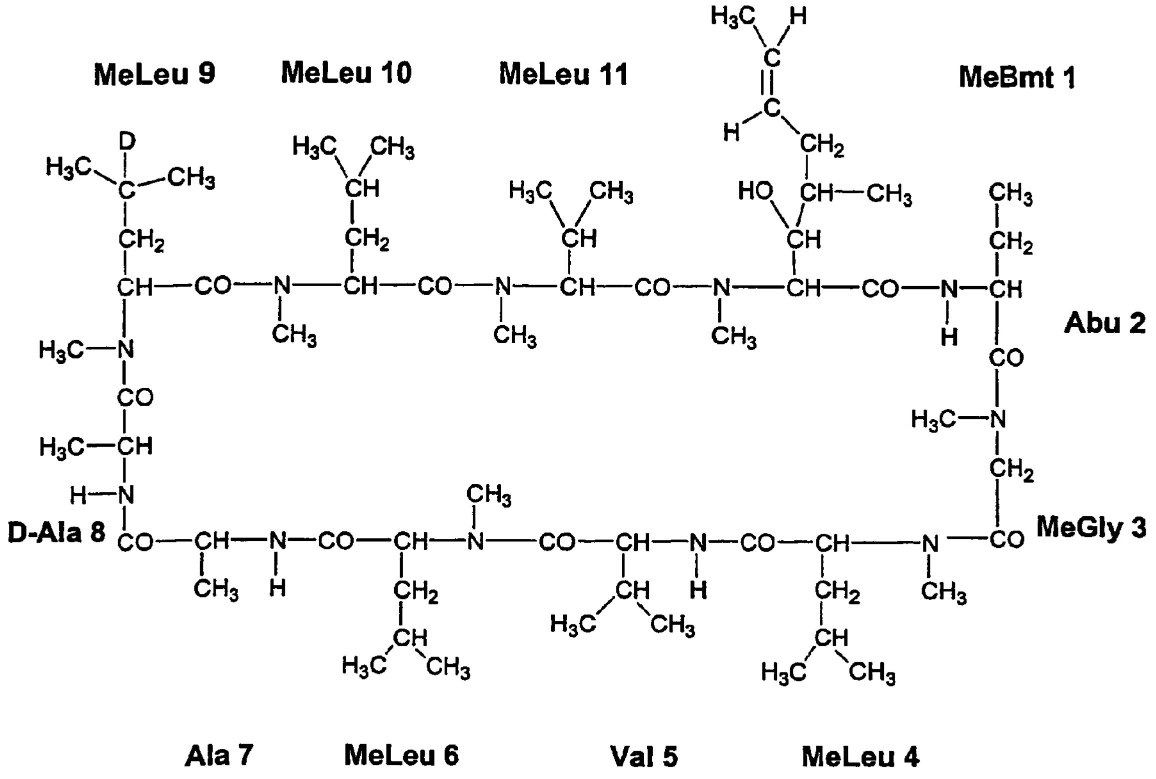
FIG. 2 is the structure of cyclosporine A showing a site of deuteration at the amino acid 9 position.

Substitution of deuterium for ordinary hydrogen and deuterated substrates for protio metabolites can produce profound changes in biosystems. Isotopically altered drugs have shown widely divergent pharmacological effects. Pettersen et al., found increased anti-cancer effect with deuterated 5,6-benzylidene-d1-L-ascorbic acid (Zilascorb) [Anticancer Res. 12, 33 (1992)].

Substitution of deuterium in methyl groups of cyclosporine will result in a slower rate of oxidation of the C-D bond relative to the rate of oxidation of a non-deuterium substituted C—H bond. The isotopic effect acts to reduce formation of demethylated metabolites and thereby alters the pharmacokinetic parameters of the drug. Lower rates of oxidation, metabolism and clearance result in greater and more sustained biological activity. Deuteration is targeted at various sites of the cyclosporin molecule to increase the potency of drug, reduce toxicity of the drug, reduce the clearance of the pharmacologically active moiety and improve the stability of the molecule.

Isotopic Substitution:

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound. (Blake et al. J. Pharm. Sci. 64, 3, 367-391, 1975). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching". It is also observed that one of the most important metabolic pathways of compounds containing aromatic systems is hydroxylation leading to a phenolic group in the 3 or 4 position to carbon substituents. Although this pathway involves cleavage of the C—H bond, it is often not accompanied by an isotope effect, because the cleavage of this bond mostly not involved in the rate limiting step. The substitution of hydrogen by deuterium at the stereo center will induce a greater effect on the activity of the drug.

Synthesis of Cyclosporine Derivatives:

The staring material for the preparation of the compounds of this invention is cyclosporine A. The process for preparing the compounds of the present invention are illustrated as shown in scheme I in FIG. 3. It will be readily apparent to one of ordinary skill in the art reviewing the synthetic route depicted below that other compounds with formula I can be synthesized by substitution of appropriate reactants and agents in the synthesis shown below.

Figure 4:
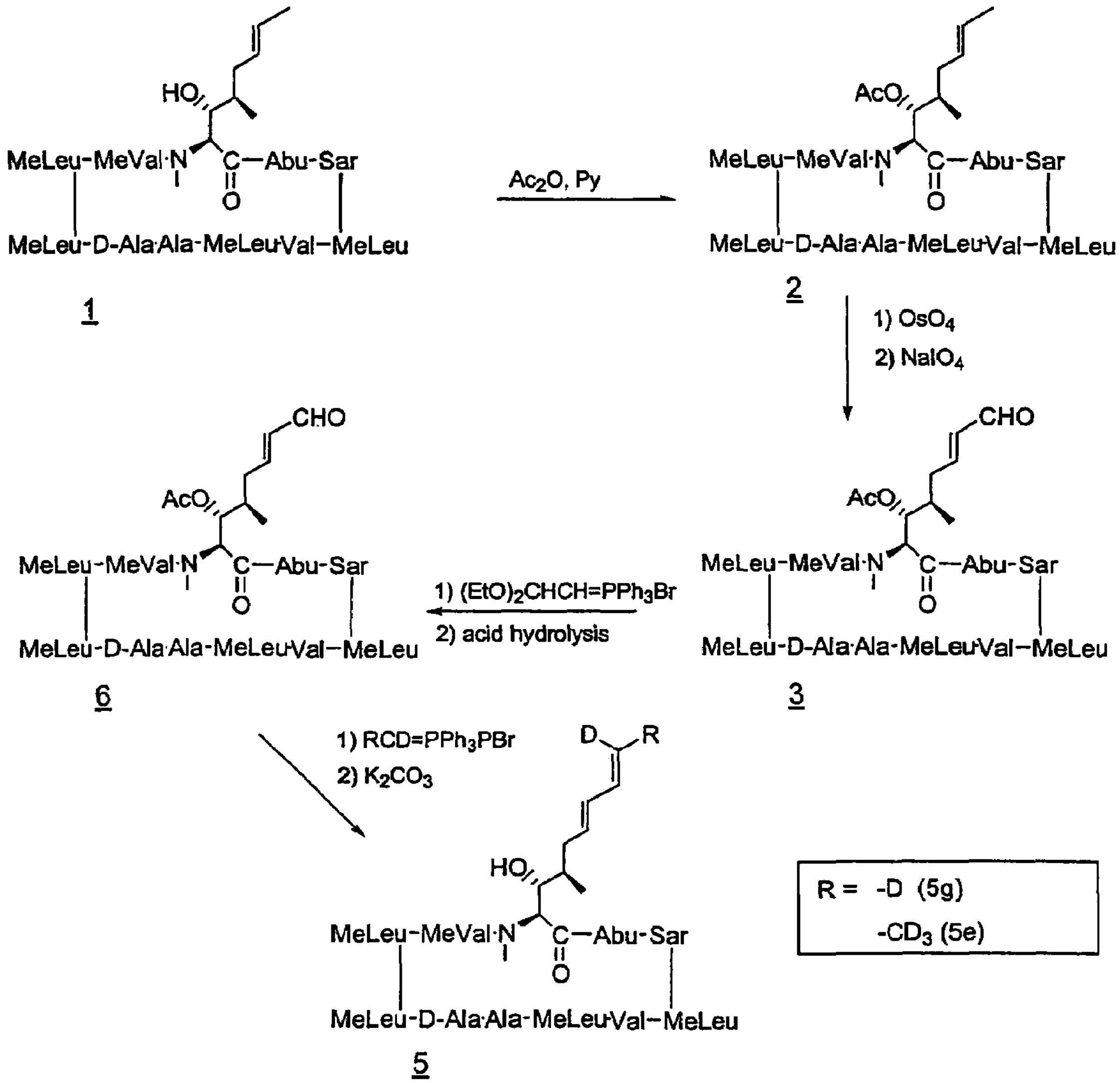
FIG. 4 is scheme II of the synthesis of the cyclosporine derivatives.

The first step in the process for making deuterated cyclosporin analogs is the preparation of the key intermediate 3 and 6. This can be achieved by the oxidation of the double bond in the amino acid 1. Treatment of cyclosporin with acetic anhydride and excess of dimethylaminopyridine provided the hydroxyl protected acetyl cyclosporine 2. Although cleavage of the double bond could then be accomplished by treatment of 2 with ozone, or $KMnO_4/NaIO_4$, it was found out that $OsO_4/NaIO_4$ was the reagent of choice for the transformation to the aldehyde product 3. The reaction was generally found to be cleaner, producing the required material and to proceed in higher yield. The drawback to this reaction is that $OsO_4$, is expensive and highly toxic, so that its use is limited. But the results can be accomplished more economically by the use of $H_2O$, with $OsO_4$ present in catalytic amounts. t-butyl hydroxide in alkaline solution and N-methylmorpholine-N-oxide can be substituted for $H_2O_2$ in this process. The aldehyde compound 3 was further treated with various deuterated alkyl or aryl triphenyl phosphonium derivatives (Wittig reagents) and hydrolysis by alkaline solution provided the final derivatives (5a-h). We also developed a general procedure to obtain various compounds as shown in Scheme II in FIG. 4.

In this approach, the aldehyde derivative 3 was treated with the Wittig reagent prepared by using standard procedure. The resultant product on mild acid hydrolysis provided the key intermediate aldehyde product 6. This was further treated with second deuterated alkyl or aryl triphenylphosphonium halide reagents and on mild acid hydrolysis yielded the required products. This method provides control over the extension of the diene system. By using this approach, olefinic double bonds can be introduced step by step.

A third approach to prepare the deuterated compounds 5a-h—is by heating non deuterated cyclosporin analogs described earlier, in a deuterated solvent such as deuterated water, deuterated acetic acid in the presence of acid or base catalyst.

Preferred cyclosporins of the present invention include those which contain a deuterium and/or a chemical substitution on amino acid 1 such as those of formula II:

(II)

X-Abu-Sar-MeLeu-Val-MeLeu-Ala-(D)Ala-MeLeu-MeLeu-MeVal
1 2 3 4 5 6 7 8 9 10 11

Where X is

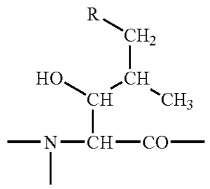

And R=—CHO, —CDO, —CH=CD-$CD_3$, —CD=CD-$CD_3$, —CH=CH—CH=CD-$CD_3$, —CD=CH—CD=CD-$CD_3$, —CH=CH—CH=$CD_2$, —CD=CH—CD=$CD_2$, —CH=$CD_2$, —CH=$CH_2$—CD=$CD_2$, —CH=CH—$CD_3$, —CH=CH—CH=CH—$CH_3$, and —CH=CH—CH=$CH_2$. Other preferred embodiments of the invention include compounds where R of above formula (I) equals -D, —CHO, —CDO, —$CD_3$, —CH=CD-$CD_3$, —CD=CD-$CD_3$, —CH=CH—CH=CD-$CD_3$, —CD=CH—CD=CD-$CD_3$, —CH=CH—CH=$CD_2$, —CD=CH—CD=$CD_2$, —CH=$CD_2$, —CD=$CD_2$, —CH=$CH_2$, —CH=CH—$CD_3$, —CH=CH—$CH_3$, —CH=CH—CH=CH—$CH_3$, and —CH=CH—CH=$CH_2$.

EXAMPLES

Example 1

To a stirred solution of cyclosporine 1 (1.01 g, 0.84 mmol) in acetic anhydride (20 mL) at room temperature was added DMAP (150 mg, 1.23 mmol, 1.5 eq). After stirring overnight, the reaction mixture was partitioned between EtOAc (50 ml) and water (25 ml). The separated EtOAc layer was then washed with water (50 mL) and brine (50 mL), dried ($MgSO_4$) and the solvent removed in vacuo to give the crude product as a glassy solid. Purification by flash chromatography through a short column of silica (2% MeOH/DCM) and lyophilisation from benzene yielded 2 (1.044 g, 0.84 mmol, quant.) as a fluffy, colourless solid; $[\alpha]_D^{25\ l}$ ‾305:7 (c. 03, $CHCl_3$); $\nu_{max}$ ($CHCl_3$ cast)/$cm^{-1}$ 3328 m, 2963 m, 1746 m, 1627 s, 1528 m, 1472 m, 1233 m; $\delta_H$ (600 MHz, $C_6D_6$) 8.73 (1H, d,J=9.5 Hz,NH), 8.30(1H,d, J=7.0 Hz,NH), 7.92(1H,d, J=7.5 Hz, NH), 7.49(1H,d,J=7.5 Hz,NH), 6.05 (1H, d, J=11.5 Hz), 5.88 (1H, dd, J=3.5, 11.5 Hz), 5.82 (1H,d,J=11.5 Hz), 5.65 (1H, dd, J=4.0, 12.0 Hz), 5.60 (IH, dd, J=3.5, 12.5 Hz), 5.63-5.57 (1H, m), 5.51-5.45 (1H, m), 5.37 (1H, dd, J=5.5, 8.5 Hz), 5.05-5.01 (2H, complex), 4.99 (1H, d, J=11.0 Hz), 4.76 (1H, p, J=7.0 Hz), 4.58 (1H, p, J=7.0 Hz), 4.02 (1H, d, J=13.5 Hz), 3.47 (3H, s), 3.30 (3H, s), 3.17 (3H, s), 3.11 (3H, s), 2.98 (3H, s), 2.68-2.62 (1H, m), 2.63 (3H, s), 2.51-2.39 (2H, complex), 2.34-2.25 (8H, complex), 2.03 (3H, s), 1.97-1.85 (2H, complex), 1.83 (3H, dd, J=1.0, 6.5 Hz), 1.82-1.77 (2H, complex), 1.68-1.61 (3H, complex), 1.55 (3H, d, J=7.0 Hz), 1.55-1.51 (1H, m), 1.44-138 (1H, m), 1.32-1.20 (5H, complex), 1.29 (3H, d, J=7.0 Hz), 1.21 (3H, d, J=6.5 Hz), 1.17 (3H, d, J=6.5 Hz), 1.14 (3H, d, J=6.5 Hz), 1.08 (3H, d, J=6.5 Hz), 1.04 (3H, d, J=6.0 Hz), 1.03 (3H,d,J=7.0 Hz), 1.00 (3H, d, J=7.0 Hz), 0.93 (3H, d, J=6.0 Hz), 0.92(3H, d, J=6.5 Hz), 0.88-0.84 (9H, complex), 0.76 (3H, d, J=6.5 Hz), 0.57 (3H, d, J=6.5 Hz); $\delta_c$ (75 MHz, $C_6D_6$) 173.6, 173.2, 172.8, 172.6, 171.3, 171.1, 170.71, 170.67, 170.4, 170.2, 169.8, 167.9 (C=O), 129.0, 126.2 (C=C), 73.1 (COAc), 58.1, 57.1, 56.0, 55.0, 54.6, 54.2 50.3, 49.9, 48.6, 48.1, 47.8, 44.5, 40.8, 39.1, 35.7, 33.6, 32.9, 32.1, 31.5, 31.2, 30.0, 29.7, 29.5, 29.3, 24.9, 24.6, 24.4, 24.0, 23.6, 23.4, 23.3, 21.7, 21.1, 21.0, 20.6, 20.3, 19.5, 18.5, 18.0, 17.7, 17.5, 17.4, 14.9, 9.7; m/z (Electrospray)

Example 2

To a solution of compound 2 (289 mg, 0.23 mmol) in a 1:1 mixture of dioxane and water (5 mL) was added firstly sodium metaperiodate (100 mg, 0.47 mmol, 2 eq) and secondly a solution of osmium tetraoxide (5 mL; 0.5 g $OsO_4$ in 250 mL of solvent). Two-phase work-up, purification by flash column chromatography (40% acetone in petroleum ether) and lyophilisation from benzene gave compound 3. (226 mg, 0.18 mmol, 80%) as a fluffy, colourless solid; $[\alpha]_D^{25}$-260.0 (c. 0.1, $CHCl_3$); $\nu_{max}$, ($CHCl_3$ cast)/$cm^{-1}$ 3325 m, 2962 m, 1748 w, 1724 w, 1677 m, 1626 s, 1228 m, 755 m; $\delta_H$ (300 MHz, $C_6D_6$) 8.63 (1H, d, J=9.5 Hz, NH), 8.16 (1H, d, J=7.0 Hz, NH), 7.95 (IH, d, J=7.5 Hz, NH), 7.48 (1H, d, J=9.0 Hz, NH), 5.93(1H, d, J=7.5 Hz), 5.84(1H, dd, J=4.0, 11.5 Hz), 5.70 (IH, d, J=11.5 Hz), 5.56-5.54 (IH, m), 5.32 (1H, dd, J=5.5, 8.0 Hz), 5.07-4.88 (3H, complex), 4.72 (1H, p, J=7.0 Hz), 4.49 (1H, p, J=7.0 Hz), 3.98 (1H, d, J=14.0 Hz), 3.42 (3H, s, $CH_3N$), 3.27 (3H, s, $CH_3N$), 3.12 (3H, s, $CH_3N$), 3.07 (3H, s, $CH_3N$), 2.91 (3H, s, $CH_3N$), 2.79 (3H, s, $CH_3N$), 2.59 (3H, s, $CH_3N$), 2.42-2.08 (10H, complex), 1.94 (3H, s, $CH_3CO_2$), 1.47 (3H, d, J=7.0 Hz), 1.24 (3H, 7.0 Hz), 1.14-1.09 (9H, complex), 1.04 (3H, d, J=6.5 Hz), 1.01 (3H, d, J=7.0 Hz), 0.96 (3H, d, J=6.5 Hz), 0.92 (3H, d, J=6.5 Hz), 0.91 (3H, d, J=6.5 Hz), 0.89 (3H, d, J=6.0 Hz), 0.83 (6H, d, J=6.5 Hz), 0.74 (3H, d, J=6.5 Hz), 0.59 (3H, d, J=6.5 Hz); $\delta_c$ (75 MHz, $C_6D_6$) 202.5 (CHO), 174.4, 174.0, 173.7, 172.8, 171.6, 171.5, 171.2, 171.1, 170.6, 170.2, 170.2, 168.1, 73.0, 58.7, 57.6, 56.7, 55.5, 55.0, 54.5, 49.4, 48.9, 48.5, 48.1, 45.0, 44.6, 41.3, 39.8, 38.8, 37.7, 36.2, 32.5, 32.0, 31.6, 30.9, 30.3, 30.0, 29.8, 29.6, 25.6, 25.3, 25.0, 24.8, 24.5, 24.0, 23.8, 23.4, 22.0, 21.7, 21.2, 20.5, 20.0, 19.8, 18.8, 18.5, 18.2, 17,4, 15.2, 10.0; m/z (Electrospray) 1232.8 ($MH^+$, 100%).

Example 3

Method A: To a solution of compound 3 (315 mg, 0.26 mmol) in THF (5 mL) at 0° C. was added a solution of the deutero-phosphorus ylide (2.67 mmol, ~10 eq), prepared from $d_5$-ethyltriphenylphosphonium iodide. After work-up, purification by flash column chromatography (30% to 60% acetone in PE) and HPLC (60% to 65% MeCN in water), then lyophilisation from benzene yielded compound 4 (153 mg, 0.12 mmol, 47%) as a fluffy, colourless solid.

Method B: To a stirred solution of compound 3 (287 mg, 0.23 mmol) in THF (5 mL) under Ar at −78° C. was carefully added a solution of phosphorus ylide (formed by the addition of sodium hexamethyldisilylamide (1.0M; 2.25 mL, 2.25 mmol, ~10 eq) to a suspension of $d_5$-ethyltriphenylphosphonium iodide (480 mg, 1.13 mmol, ~5 eq) in THF (10 mL) under Ar at room temperature). After stirring for 2 hr with gradual warming to room temperature, the reaction mixture was cooled to 0° C. and was quenched by the addition of 10%

AcOH/THF (10 mL). The reaction mixture was concentrated in vacuo and partitioned between water (20 mL) and EtOAc (20 mL). The aqueous layer was further extracted with EtOAc (20 mL) and the combined organic extracts were then washed with 1N HCl (20 mL) and water (20 mL), dried ($MgSO_4$) and the solvent removed in vacuo to give the crude product. Purification by flash column chromatography (40% acetone in petroleum ether) and lyophilisation from benzene yielded compound 4d (84 mg, 67 μmol, 29%) as a fluffy, colourless solid; $[\alpha]_D^{25}$ −283.0 (c. 0.1, $CHCl_3$); $\nu_{max}$ ($CHCl_3$ cast)/$cm^{-1}$ 3320 m, 3010 m, 2959 s, 2924 s, 2871 m, 2853 m, 1743 m, 1626 s, 756 s; $\delta_H$ (600 MHz, $C_6D_6$) 8.78 (1H, d, J=9.5 Hz), 8.33 (1H, d, J=7.0 Hz), 7.99 (1H, d, J=7.5 Hz), 7.59 (1H, d, J=9.0 Hz), 6.09 (1H, d, J=11.5 Hz), 5.92 (1H, dd, J=4.0, 11.0 Hz), 5.86 (1H, d, J=11.5 Hz), 5.72-5.64 (2H, complex), 5.62 (1H, dd, J=3.5, 12.5 Hz), 5.40 (1H, dd, J=5.5, 8.5 Hz), 5.10-5.02 (3H, complex), 4.80 (1H, q, J=7.0 Hz), 4.60 (1H, q, J=7.0 Hz), 4.05 (1H, d, J=14.0 Hz), 3.51 (3H, s), 3.31 (3H, s), 3.20 (3H, s), 3.13 (3H, s), 3.01 (3H, s), 2.87 (3H, s), 2.64 (3H, s), 2.45 (1H, dt, J=4.0, 12.5 Hz), 2.36-2.20 (10H, complex), 2.06 (3H, s), 1.93-1.79 (3H, complex); $\delta_D$ (84 MHz, $C_6H_6$) $\delta_C$ (125 MHz, $C_6D_6$) 174.5, 173.7, 173.6, 173.1, 171.7, 171.4, 170.9, 170.7, 170.6, 170.3, 170.0, 168.4, 130.2 (C═C), 123.8 (C═C), 73.8 (MeBmt C-3), 58.7, 58.1, 57.6, 57.1, 55.5, 55.0, 54.5, 49.4, 49.0, 48.6, 48.2, 45.0, 41.4, 39.9, 39.0, 37.8, 34.2, 33.9, 32.6, 32.3, 32.0, 31.4, 30.9, 30.8, 30.2, 30.1, 30.0, 29.9, 29.8, 29.6, 28.5, 25.6, 25.3, 25.0, 24.9, 24.8, 24.1, 23.9, 23.8, 23.6, 23.1, 22.1, 21.7, 21.4, 20.7, 20.0, 19.9, 19.8, 18.9, 18.7, 18.6, 18.3, 17.4, 15.3, 14.3, 10.2; m/z (Electrospray) 1270 ($[M+Na]^+$, 100%), 1286 ($[M+K]^+$, 20).

Example 4

To a stirred solution of 4d (84 mg, 67 μmol) in MeOH (5 mL) and water (2.5 mL) at room temperature was added potassium carbonate (99 mg, 0.72 mmol, ~10 eq). After stirring overnight, the MeOH was removed in vacuo and the aqueous residue was partitioned between EtOAc (10 mL) and 5% citric acid solution (10 mL). The EtOAc layer was then washed with water (10 mL) and brine (10 mL), dried (MgSO4) and the solvent removed in vacuo to give the crude product. HPLC purification (60% to 65% MeCN in water) and lyophilisation from benzene yielded compound 5d (59 mg, 49 μmol, 70%) as a fluffy, colourless solid; $[\alpha]_D^{25}$-262.0 (c. 0.05, $CHCl_3$); $\nu_{max}$ ($CHCl_3$ cast)/$cm^{-1}$ 3318 m, 3008 m, 2960 s, 2872 m, 1627 s, 1519 m, 1470 m, 1411 m, 1295 m, 1095 m, 754 m; $\delta_H$ (600 MHz, $C_6H_6$) 8.27 (1H, d, J=9.5 Hz), 7.96 (1H, d, J=7.5 Hz), 7.63 (1H, d, J=8.0 Hz), 7.45 (1H, d, J=9.0 Hz), 5.87 (1H, dd, J=3.5, 11.0 Hz), 5.74 (1H, d, J=7.5 Hz), 5.73-5.69 (1H, m), 5.66-5.64 (1H, br d, J=11.0 Hz), 5.79 (1H, dd, J=4.0, 11.5 Hz), 3.39 (1H, dd, J=5.5, 10.5 Hz), 5.33 (1H, dd, J=5.5, 8.5 Hz), 5.24 (1H, d, J=11.0 Hz), 5.12 (1H, dt, J=7.5, 10.0 Hz), 4.88-4.79 (3H, complex), 4.22 (1H, dd, J=5.5, 7.5 Hz), 4.00 (1H d, 13.5 Hz), 3.72 (3H, s), 3.22 (3H, s), 3.06 (3H, s), 2.97 (3H, s), 2.92 (3H, s), 2.85 (3H, s), 2.67-2.60 (1H, m), 2.58 (3H, s), 2.56-2.50 (1H, br m), 2.33-2.23 (4H, complex), 2.20-2.07 (4H, complex), 1.80-1.74 (3H, complex), 1.67 (3H, d, J=7.0 Hz), 1.56-1.50 (2H, complex), 1.46-1.23 (9H, complex), 1.17-1.13 (16H, complex), 1.06 (3H, d, J=6.5 Hz), 1.02 (3H, d, J=7.0 Hz), 0.98 (3H, d, J=6.5 Hz), 0.96 (3H, d, J=7.0 Hz), 0.92-0.89 (9H complex), 0.86 (3H, t, J=7.5 Hz), 0.83 (3H, d, J=6.0 Hz), 0.64 (3H, d, J=6.5 Hz); $\delta_D$ (84 MHz, $C_6H_6$) 1.64 ($C\underline{D}_3$); $\delta_C$(75 MHz, $C_6H_6$) 174.2, 174.1, 174.0, 173.7, 171.8, $\overline{171}$.4, 171.2, 170.5, 170.4, 170.3, 169.8, 130.2, 124.1, (99.2,) 74.3, (67.1,) 66.3, 66.1, 61.0, 59.5, 58.3, 57.8, 55.7, 55.5, 55.4, 49.4, 49.0, 48.4, 45.3, 41.4, 39.6, 39.0, 37.8, 36.5, 36.1, 35.8, 33.7, 31.6, 30.8, 30.4, 30.1, 29.9, 29.5, 29.4, 25.5, 25.2, 25.0, 24.9, 24.5, 24.2, 23.8, 23.7, 23.6, 22.0, 21.4, 20.0, 18.8, 18.5, 17.8, 16.0, 10.1; m/z (Electrospray) 1206 ($[M+H]^+$, 30%), 1228 ($[M+Na]^+$,100), 1244 ($[M+K]^+$, 25).

Example 5

To a vigorously stirred mixture of compound (49 mg, 39.8 μmol) and deuterated $d_3$-allyl triphenylphosphonium bromide (311 mg, 812 μmol, ~20 eq) in benzene (3 mL) at room temperature was added 1N NaOH (3 mL). Stirring was continued at room temperature for 5 days, after which time the 2 layers were separated, the benzene layer was washed with water (5 mL), dried ($MgSO_4$) and the solvent removed in vacuo to give the crude product. Purification by HPLC (20% to 60% MeCN in water) and lyophilisation from benzene yielded compound 4g (23 mg, 18.3 μmol, 47%) as a fluffy, colourless solid; $[\alpha]_D^{25}$-264.2 (c. 0.24, $CHCl_3$); $\nu_{max}$= ($CHCl_3$ cast)/$cm^{-1}$ 3322 m, 2959 m, 1744 m, 1626 s, 1231 m, 754 m; $\delta_H$ (300 MHz, $C_6D_6$) complex due to 1:1 ratio of geometrical isomers 8.73 (d, J=9.5 Hz, N$\underline{H}$), 8.72 (d, J=9.5 Hz, N$\underline{H}$), 8.29 (d, J=6.5 Hz, N$\underline{H}$), 8.26 (d, J=6.5 Hz, N$\underline{H}$), 7.92 (d, J=7.5 Hz, N$\underline{H}$), 7.86 (d, J=7.5 Hz, N$\underline{H}$), 7.53 (d, J=9.0 Hz, N$\underline{H}$), 7.49 (d, J=9.0 Hz, N$\underline{H}$), 7.10-6.70 (complex), 6.33 (br t, J=11.0 Hz), 6.18 (d, J=10.5 Hz), 6.12 (d, J=10.5 Hz), 6.05 (d, J=11.0 Hz), 6.03 (d, J=11.0 Hz), 5.90-5.53 (complex), 5.37 (dd, J=6.0, 8.0 Hz), 5.20 (d, J=12.0 Hz), 5.14 (d, J=12.0 Hz), 5.07-4.97 (complex), 4.80-4.70 (complex), 4.57 (p, J=7.0 Hz), 4.02 (d, J=14.0 Hz), 4.01 (d, J=14.0 Hz), 3.47 (s), 3.46 (s), 3.28 (s), 3.26 (s), 3.16 (s), 3.15 (s), 3.09 (s), 2.97 (s), 2.96 (s), 2.84 (s), 2.62 (s), 2.48-2.23 (complex), 2.05 (s), 2.03 (s), 1.95-1.59 (complex), 1.54 (d, J=7.0 Hz), 1.53-0.80 (complex), 0.77 (d, J=6.5 Hz), 0.58 (d, J=6.5 Hz), 0.57 (d, J=6.5 Hz); $\delta_C$ (75 MHz, $C_6D_6$) 174.5, 174.0, 173.9, 173.6, 173.5, 173.1, 17.7, 171.6, 171.4, 170.9, 170.8, 170.6, 170.6, 170.3, 169.8, 169.7, 168.4, 137.9, 133.9, 133.5, 132.8, 132.3, 131.6, 130.1, 116.9, 115.0, 73.6, 58.6, 57.6, 57.0, 56.8, 55.7, 55.5, 55.0, 54.9, 54.7, 54.5, 49.4, 48.9, 48.5, 48.2, 48.1, 44.9, 41.5, 39.9, 39.0, 38.9, 37.8, 37.6, 36.6, 36.3, 34.1, 33.7, 32.7, 32.1, 32.0, 31.5, 30.9, 30.7, 30.0, 29.8, 29.6, 25.6, 25.5, 25.3, 25.2, 25.0, 24.9, 24.1, 23.9, 23.7, 23.6, 22.1, 21.7, 21.6, 21.4, 21.3, 20.7, 20.0, 19.9, 18.9, 18.6, 18.3, 17.6, 15.3, 10.2; m/z (Electrospray) 1258.8 ($MH^+$, 100%).

Example 6

To a vigorously stirred mixture of compound 3 (56 mg, 45.5 μmol) and deuterated $d_4$-crotyl triphenylphosphonium bromide (360 mg, 907 μmol, ~20 eq) in benzene (3 mL) at room temperature was added 1N NaOH (3 mL). Stirring was continued at room temperature for 5 days, after which time the 2 layers were separated, the benzene layer was washed with water (5 mL); dried (MgSO4) and the solvent removed in vacuo to give the crude product. Purification by HPLC (20% to 60% MeCN in water) and lyophilisation from benzene yielded compound 4e (23 mg, 18.1 μmol, 40%) as a fluffy, colourless solid; $[\alpha]_D^{25}$-236.0 (c. 0.25, $CHCl_3$); $\nu_{max}$ ($CHCl_3$ cast)/$cm^{-1}$ 3324 m, 2959 m, 2871 m, 1745 w, 1626 s, 1231 m; $\delta_H$ (300 MHz, $C_6D_6$) complex due to presence of 4 isomers 8.76 (d, J=6.0 Hz), 8:73 (d, J=6.0 Hz), 8.29 (d, J=7.0 Hz), 7.93 (d, J=7.5 Hz), 7.88 (d, J=7.5 Hz), 7.53 (d, J=9.5 Hz), 7.62-7.31(1H, complex), 7.16-6.88 (2H, complex), 6.59-6.39 (complex), 6.28 (t, J=11.0 Hz), 6.15 (d, J=10.5 Hz), 6.09 (d, J=10.5 Hz), 6.05 (d, J=11.5 Hz), 6.03 (d, J=11.5 Hz), 5.90-5.82 (complex), 5.68-5.35 (complex), 5.08-4.97 (complex), 4.81-4.72 (complex), 4.63-4.53 (complex), 4.03 (d, J=14.0 Hz), 3.47 (s), 3.46 (s), 3.28 (s), 3.26 (s), 3.17 (s), 3.15 (s), 3.09 (s), 2.98 (s), 2.97 (s), 2.83 (s), 2.63 (s), 2.62 (s) 2.71-2.56 (complex), 2.47-2.23 (complex), 2.05 (s), 2.04 (s), 2.03 (s), 2.02 (s), 1.98-0.82 (complex), 0.77 (d, J=6.5 Hz), 0.58 (d, J=6.5 Hz), 0.58 (d, J=6.5 Hz); m/z (Electrospray) 1273.8 ($MH^+$, 100%).

Example 7

To a stirred solution of compound 4g (20 mg, 15.9 μmol) in methanol (5 mL) and water (1 mL) at room temperature was added potassium carbonate (30 mg, 217 μmol). After stirring overnight, the reaction mixture was partitioned between EtOAc (10 mL) and 5% aqueous citric acid (10 mL). The aqueous layer was further extracted with EtOAc (5 mL), the combined organic layers were then washed with 5% citric acid (10 mL) and brine (10 mL), dried ($MgSO_4$) and the solvent removed in vacuo to give the crude product. Purification by HPLC (65% MeCN) and lyophilisation from benzene yielded compound 5g (10 mg, 82 μmol, 52%) as a fluffy, colourless solid; $[\alpha]_D^{25}$-285.2 (c. 0.29, $CHCl_3$); $\nu_{max}$ ($CHCl_3$ cast)/$cm^{-1}$ 3500-3200 br, 3319 m, 2958 m, 2927 m, 1626 s, 1520 m, 1468 m, 754 m; $\delta_H$ (300 MHz, $C_6D_6$) complex due to the presence of 2 isomers 8.25 (d, J=10.0 Hz, NH), 8.13 (d, J=10.0 Hz, NH), 7.93 (d, J=7.0 Hz, NH), 7.84 (d, J=7.0 Hz, NNH), 7.67 (d, J=8.0 Hz, NH), 7.61 (d, J=8.0 Hz, NH), 7.55 (d, J=8.5 Hz, NH), 7.54 (d, J=8.5 Hz, NH), 6.84 (t, J=10.5 Hz), 6.79 (t, J=10.5 Hz), 6.58 (t, J=10.5 Hz), 6.52 (t, J=10.5 Hz), 6.30-6.14 (complex), 5.88-5.78 (complex), 5.75-5.66 (complex), 5.44-4.74 (complex), 4.22-4.15 (complex), 3.95 (d, J=14.0 Hz), 3.93 (d, J=14.0 Hz), 3.72 (s), 3.68 (s), 3.19 (s), 3.17 (s), 3.05 (s), 3.03 (s), 2.94 (s), 2.93 (s), 2.89 (s), 2.86 (s), 2.82 (s), 2.81 (s), 2.72-2.53 (complex), 2.55 (s), 2.54 (s), 249-2.36 (complex), 2.32-2.03 (complex), 1.81-0.81 (complex), 0.65 (d, J=6.5 Hz)), m/z (Electrospray) 1216.8 ($MH^+$, 100%), 607.9 ($[M+2H]^{2+}$, 15).

Example 8

To a stirred solution of compound 4e (18 mg, 14.2 μmol) in methanol (5 mL) and water (1 mL) at room temperature was added potassium carbonate (35 mg, 254 μmol). After stirring overnight, the reaction mixture was partitioned between EtOAc (10 mL) and 5% aqueous citric acid (10 mL). The aqueous layer was further extracted with EtOAc (5 mL), the combined organic layers where then washed with 5% citric acid (10 mL) and brine (10 mL), dried ($MgSO_4$) and the solvent removed in vacuo to give the crude product. Purification by HPLC (65% MeCN) and lyophilisation from benzene yielded compound 5e (10 mg, 8.1 μmol, 57%) as a fluffy, colourless solid $[\alpha]_D^{25}$-285.5(c. 0.11, $CHCl_3$); $\delta_H$ (300 MHz, $C_6D_6$) complex due to presence of 4 isomers 8.31 (d, J=9.5 Hz), 8.28 (d, J=9.5 Hz), 8.14 (d, J=9.5 Hz), 7.96 (d, J=7.5 Hz), 7.95 (d, J=7.5 Hz), 7.86 (d, J=7.5 Hz), 7.85 (d, J=7.5 Hz), 7.63 (d, J=7.5 Hz), 7.59 (d, J=75 Hz), 7.50-7.44 (complex), 6.60-6.49 (complex), 6.32-6.11 (complex), 5.88-5.83 (complex), 5.76-5.71 (complex), 5.64-5.22 (complex), 5.17-5.08 (complex), 4.91-4.77 (complex), 4.26-4.18 (complex), 3.99 (d, J=14.0 Hz), 3.97 (d, J=14.0 Hz), 3.74(s), 3.73(s), 3.71 (s), 3.69 (s), 3.22 (s), 3.21 (s), 3.20 (s), 3.19 (s), 3.07 (s), 3.06 (s), 3.05 (s), 2.97 (s), 2.96 (s), 2.95 (s), 2.92 (s), 2.91 (s), 2.89 (s), 2.84 (s), 2.83 (s), 2.69-2.07 (complex), 2.58 (s), 2.57 (s), 1.84-0.81 (complex), 0.64 (d, J=6.5 Hz); m/z (Electrospray) 1269.8 ([M+K]+, 5%), 1253.8 ($[M+Na]^+$, 30), 1231.8 ($MH^+$)

Example 9

The immunosuppressive activity can be tested for cyclosporine and the disclosed cyclosporine analogs as described below. Calcineurin activity is assayed using a modification of the method previously described by Fruman et al (A Proc Natl Acad Sci USA, 1992). Whole blood lysates are evaluated for their ability to dephosphorylate a $^{32}$P-labelled 19 amino acid peptide substrate in the presence of okadaic acid, a phosphatase type 1 and 2 inhibitor. Background phosphatase 2C activity (CsA and okadaic acid resistant activity) is determined and subtracted from each sample, with the assay performed in the presence and absence of excess added CsA. The remaining phosphatase activity is taken as calcineurin activity.

Example 10

A mixed lymphocyte reaction (MLR) assay is performed with cyclosporine and the disclosed cyclosporine analogs. The MLR assay is useful for identifying CsA derivatives with biological (immunosuppressive) activity and to quantify this activity relative to the immunosuppressive activity of the parent CsA molecule.

An example of a lymphocyte proliferation assay procedure useful for this purpose is as follows:

1. Collect blood from two individuals (20 mls each) and isolate lymphocytes using Ficoll-Paque (Pharmacia Biotech).
2. Count lymphocytes at 1:10 dilution in 2% acetic acid (v/v).
3. Prepare 10 mls of each lymphocyte populations (A+B) at $1\times10^6$ cells/ml in DMEM/20% FCS (v/v).
4. Set up a 96 well sterile tissue culture plate, flat bottom (Sarstedt, cat #83.1835). To each well add:
5. Aliquot 100 μl per well lymphocyte population A
6. Aliquot 100 μl per well lymphocyte population B
7. Aliquot 20 μl per well of drug (CSA and CSA derivatives) at 0, 2.5, 5, 10, 25, 50 and 100 μg/L in triplicate in DMEM with no supplements.
8. To measure the effect of drug on proliferation, incubate the plate for 5 days at 37° C. in 5% $CO_2$ atmosphere.
9. On day 6, prepare 3.2 mls of 1:50 dilution of Methyl-3H-Thymidine (Amersham Life Science, cat # TRK 120) in DMEM with no supplements. Add 30 μl per well and incubate for 18 hours at 37° C. in 5% $CO_2$ atmosphere.
10. On day 7 cells are harvested onto glass microfiber filters GF/A (Whatman, cat # 1820024) using a Cell-Harvestor (Skatron, cat # 11019). Wash cells 3× with 1.0-ml sterile distilled water.

Note: All procedures are done using sterile techniques in a biological flow hood.
11. Place filters in Scintilation vials and add 1.5 mls of SciniSafe Plus 50% scintilation fluid (Fisher, cat # SX-25-5).
12. Measure the amount of radioactivity incorporated in the lymphocytes using a beta counter (Micromedic System Inc., TAURUS Automatic Liquid Scintilation Counter) for 1.0 minute.
13. Calculate averages and standard deviations for each drug and express results as:

$$\%\ \text{Inhibition} = \frac{[1 - \text{Ave } CPM \text{ of test drug}]}{\text{Ave } CPM \text{ of zero drug}} \times 100$$

$$\%\ \text{Proliferation} = 100 - \%\ \text{Inhibition}$$

From the results of the calcineurin assay and the mixed lymphocyte reaction assay, it was found that cyclosporines that have been chemically substituted and/or deuterated at the amino acid 1 position can possess significant immunosupressant activity.
Example 11
Other cyclosporine derivatives of the invention which have been prepared include the following:
| STRUCTURE | CODE # |
|---|---|
| 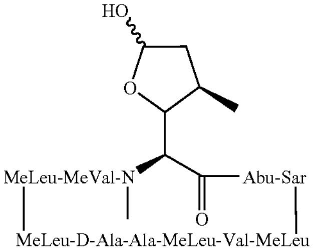 | DB-b1-01 |
| 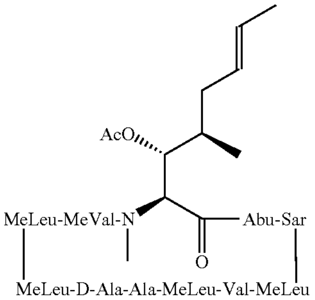 | DB-b1-08 |
| 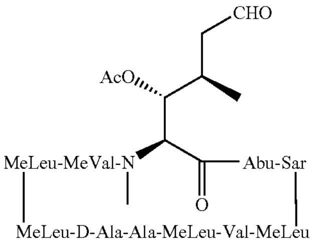 | DB1-b1-11 |
| 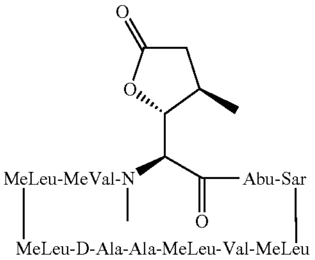 | DB1-b1-31 |
| 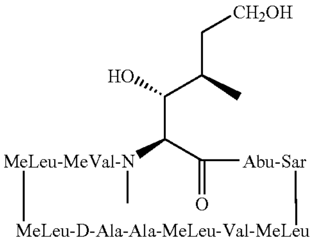 | DB1-b1-45 |
-continued
| STRUCTURE | CODE # |
|---|---|
| 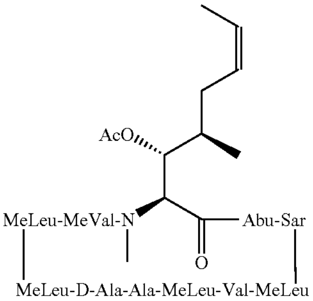 | DB1-b186C |
| 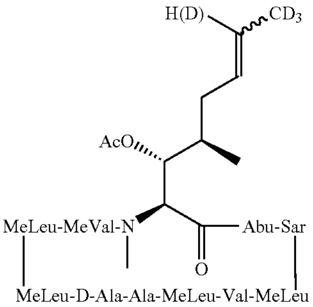 | DB-b1-92b |
| 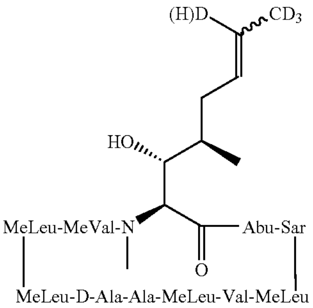 | DB-b1-93c |
| 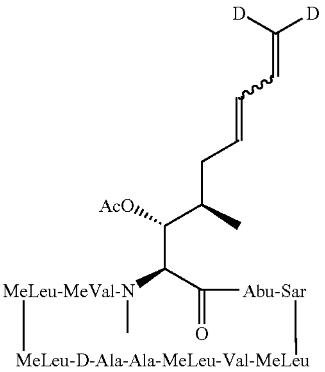 | DB-b1-145D |

-continued
| STRUCTURE | CODE # |
|---|---|
| 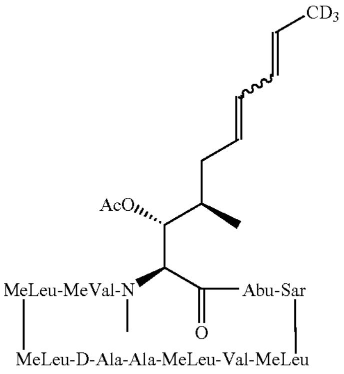 | DB-b1-147D |
| 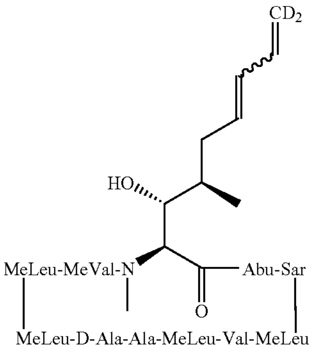 | DB-01-148 |
| 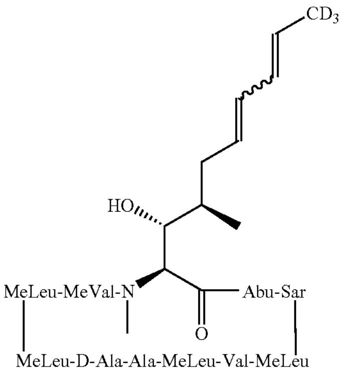 | DB-b1-151 |
| 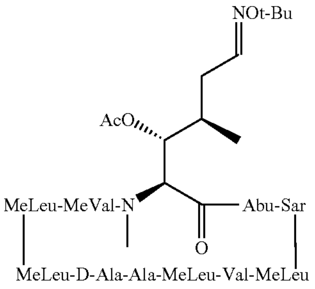 | DB-b1-176 |
-continued
| STRUCTURE | CODE # |
|---|---|
| 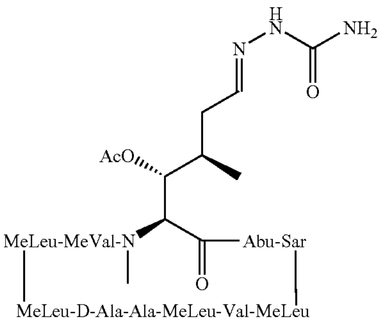 | DB-b1-179 |
| 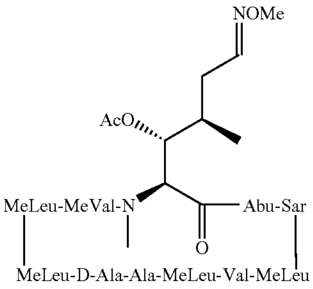 | DB-b1-180 |
| 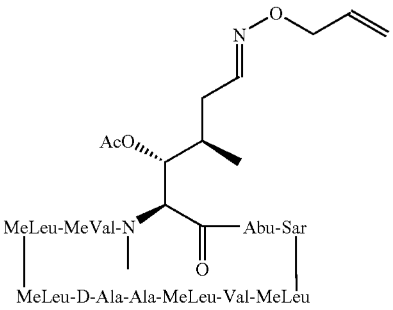 | DB-b1-192 |
| 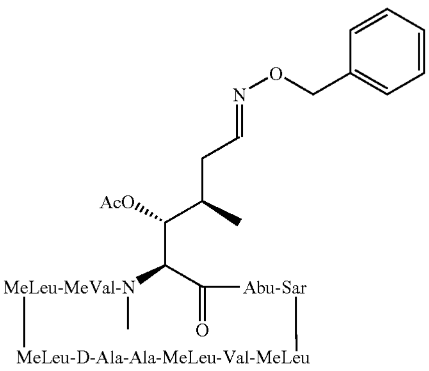 | DB-b1-193 |

-continued

| STRUCTURE | CODE # |
|---|---|
| 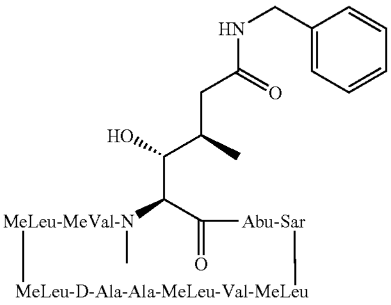 | DB-b1-134 |
| 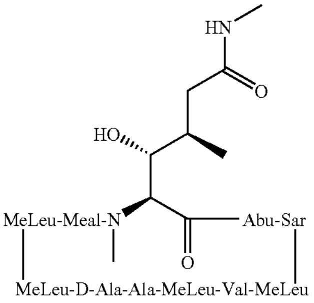 | DB-b1-194 |
| 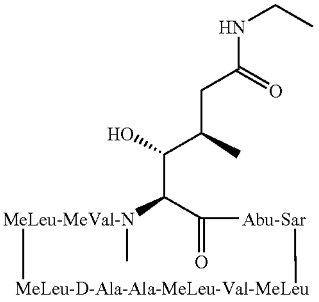 | DB-b1-195 |
| 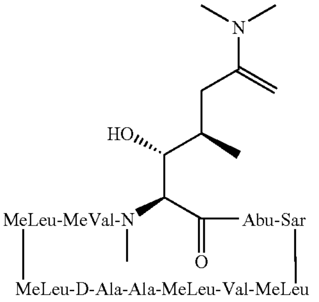 | DB-b1-196 |
| 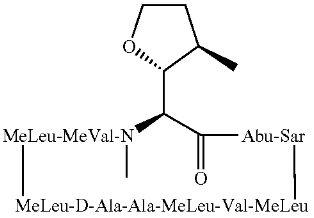 | DB-b1-50B |

Drug Composition Formulation and Elicitation of Immunosupression

Determination of the physiochemical, pharmacodynamic, toxicological and pharmacokinetic properties of the cyclosporine derivatives disclosed can be made using standard chemical and biological assays and through the use of mathematical modeling techniques which are known in the chemical and pharmacological/toxicological arts. The therapeutic utility and dosing regimen can be extrapolated from the results of such techniques and through the use of appropriate pharmacokinetic and/or pharmacodynamic models.

The compound of this invention may be administered neat or with a pharmaceutical carrier to a warm blooded animal in need thereof. The pharmaceutical carrier may be solid or liquid.

This invention also relates to a method of treatment for patients suffering from immunoregulatory abnormalities involving the administration of the disclosed cyclosporines as the active constituent.

For the treatment of these conditions and diseases caused by immunoirregularity, a deuterated cyclosporin may be administered orally, topically, parenterally, by inhalation spray or rectally in dosage unit formulations containing conventional non-toxic pharmaceutically acceptable carriers, adjuvants and vehicles. The term parenteral, as used herein, includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They be also be in the form of soft gelatin capsules wherein the active ingredient is mixed with water and oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose, aspartame or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient is admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleates, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol, aspartame or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The disclosed cyclosporines may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the disclosed cyclosporines are employed.

Dosage levels of the order from about 0.05 mg to about 50 mg per kilogram of body weight per day are useful in the treatment of the above-indicated conditions (from about 2.5 mg to about 2.5 gms. per patient per day).

The amount of active ingredient that may be combined with the carrier materials to produce a single dosage form will vary depending upon the host treated and the particular mode of administration. For example, a formulation intended for the oral administration of humans may contain from 2.5 mg to 2.5 gm of active agent compounded with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

All references listed herein are incorporated by reference. In the case of conflict, the text of the application is controlling. Modifications and changes of the disclosed compounds and methods will be apparent to one skilled in the art. Such modifications and changes are intended to be encompassed by this disclosure and the claims appended hereto.

The invention claimed is:

1. A cyclosporin A derivative having the structure of Formula (II):

(II)

Figure 3:
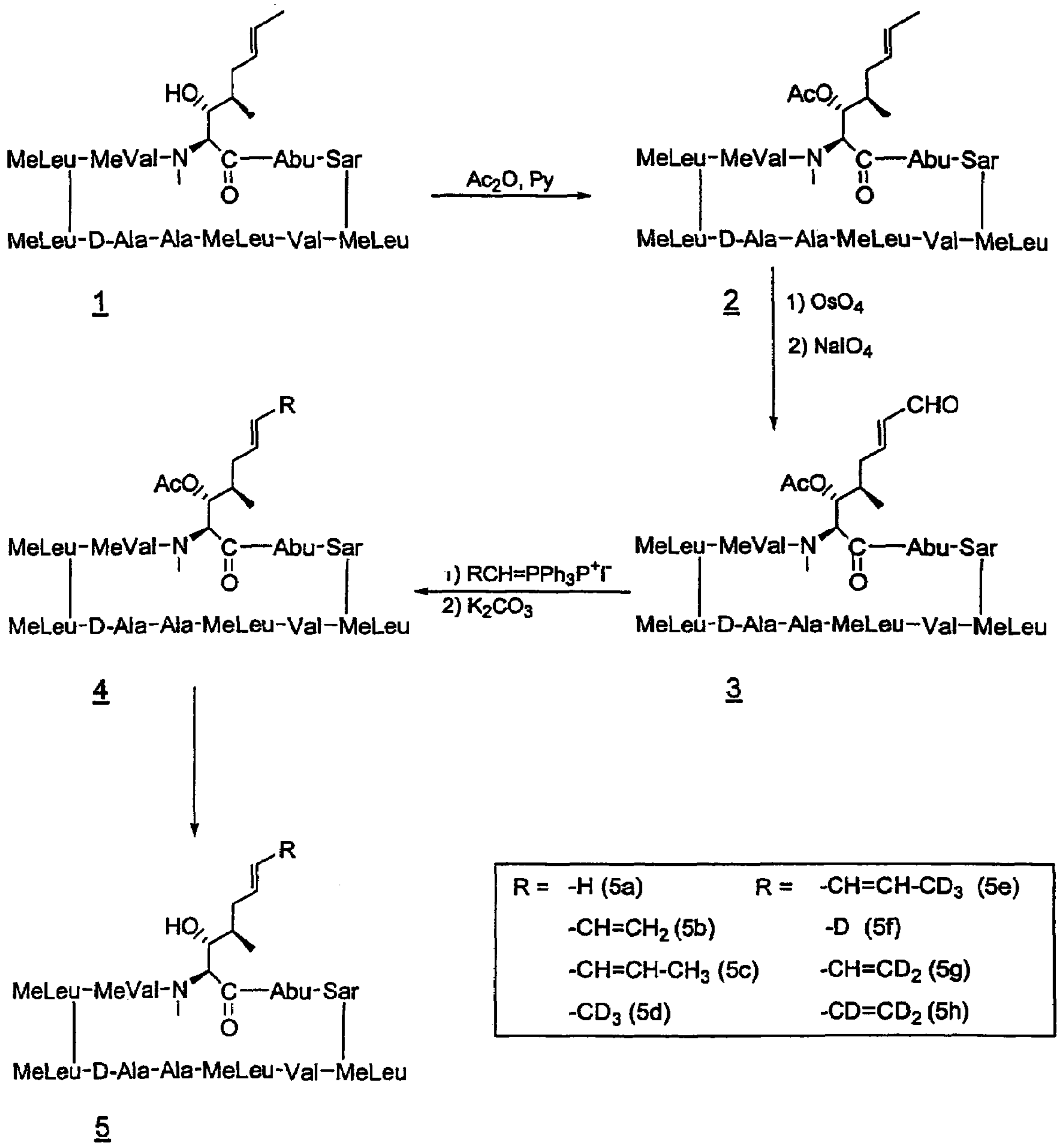
FIG. 3 is scheme I of the synthesis of the cyclosporine derivatives.

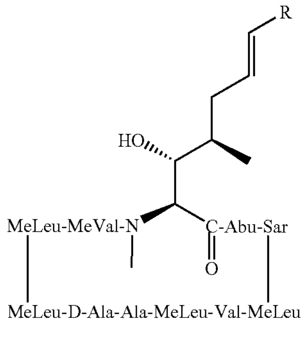

wherein the configuration of the MeBmt residue is as shown in FIG. 3, compound 5 and R is an unsaturated straight or branched aliphatic carbon chain of from 2 to 3 carbons, prepared by a method comprising:

(a) protecting the β-alcohol of cyclosporin A, thereby forming an intermediate acetyl cyclosporin A;

(b) oxidizing the acetyl cyclosporin A to produce an intermediate acetyl cyclosporin A aldehyde;

(c) treating the intermediate acetyl cyclosporin A aldehyde in a Wittig reaction with a phosphorus ylide having the structural formula $RCH{=}PPh_3$ wherein R is as defined above to produce an acetyl cyclosporin A derivative having the structure of Formula (I):

(I)

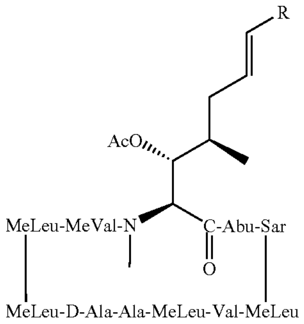

wherein R is as defined above and the configuration of the MeBmt residue is as shown in FIG. 3, compound 5; and (d) hydrolyzing the acetyl cyclosporin A derivative having the structure of Formula (I) with a base.

2. The cyclosporin A derivative of claim 1, wherein the oxidizing step is carried out with an oxidizing agent selected from the group consisting of ozone, potassium permanganate, and osmium tetroxide.

3. The cyclosporin A derivative of claim 2, wherein the oxidizing agent is osmium tetroxide.

4. A cyclosporine A derivative having the structure of Formula (II):

(II)

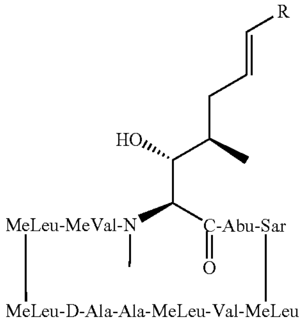

wherein the configuration of the MeBmt residue is as shown in FIG. 3, compound 5 and R is a saturated or unsaturated, straight or branched, aliphatic carbon chain of from 2 to 3 carbons that is substituted with one or more deuterium atoms, prepared by the method comprising the steps of:

(a) protecting the β-alcohol of cyclosporin A , thereby forming an intermediate acetyl cyclosporin A;

(b) oxidizing the acetyl cyclosporin A to produce an intermediate acetyl cyclosporin A aldehyde;

(c) treating the intermediate acetyl cyclosporin A aldehyde in a Wittig reaction with a phosphorus ylide having the structural formula $RCH{=}PPh_3$ to produce an acetyl cyclosporine A derivative having the structure of Formula (I):

(I)

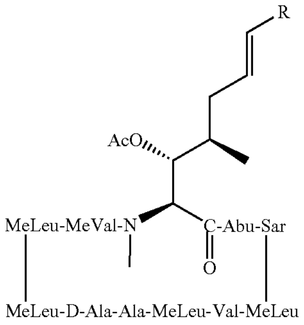

wherein the configuration of the MeBmt residue is as shown in FIG. 3, compound 5; and (d) hydrolyzing the acetyl cyclosporin A derivative having the structure of Formula (I) with a base.

5. The cyclosporin A derivative of claim 4, wherein the oxidizing step is carried out with an oxidizing agent selected from the group consisting of ozone, potassium permanganate, and osmium tetroxide.

6. The cyclosporin A derivative of claim 5, wherein the oxidizing agent is osmium tetroxide.

7. A cyclosporin A derivative having the structure of Formula (II):

(II)

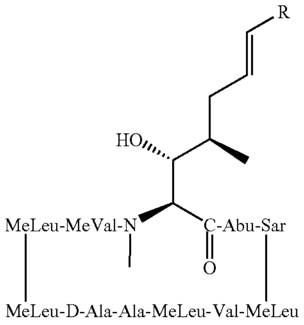

wherein the configuration of the MeBmt residue is as shown in FIG. 3, compound 5 and R is a member selected from the group consisting of —D, $—CH{=}CD\text{-}CD_3$, $—CD{=}CD\text{-}CD_3$, $—CH{=}CH—CH{=}CD\text{-}CD_3$, $CD{=}CH—CD{=}CD\text{-}CD_3$, $—CH{=}CHCH{=}CD_2$, $—CD{=}CH—CD{=}CD_2$, $—CH{=}CD_2$, $—CD{=}CD_2$, $—CH{=}CH_2$, $—CH{=}CH—CD_3$, $—CH{=}CH—CH_3$, $—CH{=}CH—CH{=}CH—CH_3$, and $—CH{=}CH—CH{=}CH_2$ prepared by a method comprising:

(a) protecting the β-alcohol of cyclosporin A , thereby forming an intermediate acetyl cyclosporin A;

(b) oxidizing the acetyl cyclosporin A to produce an intermediate acetyl cyclosporin A aldehyde;

(c) treating the intermediate acetyl cyclosporin A aldehyde in a Wittig reaction with a phosphorus ylide having the structural formula $RCH{=}PPh_3$ to produce an acetyl cyclosporin A derivative having the structure of Formula (I):

(I)

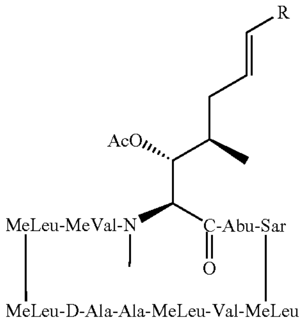

wherein the configuration of the MeBmt residue is as shown in FIG. 3, compound 5; and (d) hydrolyzing the acetyl cyclosporin A derivative having the structure of Formula (I) with a base.

8. The cyclosporin A derivative of claim 7, wherein the oxidizing step is carried out with an oxidizing agent selected from the group consisting of ozone, potassium permanganate, and osmium tetroxide.

9. The cyclosporin A derivative of claim 8, wherein the oxidizing agent is osmium tetroxide.

* * * * *